(12) United States Patent
Askari et al.

(10) Patent No.: US 10,227,289 B2
(45) Date of Patent: Mar. 12, 2019

(54) METHODS FOR TREATING DISEASES OF THE LUNG

(75) Inventors: Syed H. Askari, San Jose, CA (US); George Horng, Millbrae, CA (US)

(73) Assignee: MEDICUS BIOSCIENCES, LLC, San Francisco, CA (US)

( * ) Notice: Subject to any disclaimer, the term of this patent is extended or adjusted under 35 U.S.C. 154(b) by 0 days.

(21) Appl. No.: 13/696,028

(22) PCT Filed: May 6, 2011

(86) PCT No.: PCT/US2011/035640
§ 371 (c)(1),
(2), (4) Date: Jan. 16, 2013

(87) PCT Pub. No.: WO2011/140517
PCT Pub. Date: Nov. 10, 2011

(65) Prior Publication Data
US 2013/0108711 A1    May 2, 2013

Related U.S. Application Data

(60) Provisional application No. 61/332,197, filed on May 7, 2010, provisional application No. 61/378,730, filed on Aug. 31, 2010, provisional application No. 61/387,841, filed on Sep. 29, 2010.

(51) Int. Cl.
| C07C 229/24 | (2006.01) |
| --- | --- |
| A61K 9/00 | (2006.01) |
| A61K 49/04 | (2006.01) |
| A61K 47/34 | (2017.01) |
| C08G 65/34 | (2006.01) |

(52) U.S. Cl.
CPC .......... *C07C 229/24* (2013.01); *A61K 9/0002* (2013.01); *A61K 9/0078* (2013.01); *A61K 47/34* (2013.01); *A61K 49/04* (2013.01); *C08G 65/34* (2013.01)

(58) Field of Classification Search
None
See application file for complete search history.

(56) References Cited

U.S. PATENT DOCUMENTS

| | | |
|---|---|---|
| 5,037,384 A | 8/1991 | Chang |
| 5,135,755 A | 8/1992 | Czech et al. |
| 5,336,175 A | 8/1994 | Mames |
| 5,858,345 A | 1/1999 | Charles et al. |
| 5,874,500 A | 2/1999 | Rhee et al. |
| 6,051,648 A | 4/2000 | Rhee et al. |
| 6,135,118 A | 10/2000 | Dailey |
| 6,149,931 A | 11/2000 | Schwartz et al. |
| 6,153,211 A | 11/2000 | Hubbell et al. |
| 6,180,687 B1 | 1/2001 | Hammer et al. |
| 6,207,772 B1 | 3/2001 | Hatsuda et al. |
| 6,312,725 B1 | 11/2001 | Wallace et al. |
| 6,458,889 B1 * | 10/2002 | Trollsas et al. ............. 525/54.1 |
| 6,475,508 B1 | 11/2002 | Schwartz et al. |
| 6,547,714 B1 | 4/2003 | Dailey |
| 6,566,406 B1 | 5/2003 | Pathak et al. |
| 6,605,294 B2 | 8/2003 | Sawhney |
| 6,624,245 B2 | 9/2003 | Wallace et al. |
| 6,632,457 B1 | 10/2003 | Sawhney |
| 6,703,037 B1 | 3/2004 | Hubbell et al. |
| 6,703,378 B1 | 3/2004 | Kunzler et al. |
| 6,818,018 B1 | 11/2004 | Sawhney |
| 7,009,343 B2 | 3/2006 | Lim et al. |
| 7,255,874 B1 | 8/2007 | Bobo et al. |
| 7,332,566 B2 | 2/2008 | Pathak et al. |
| 7,553,810 B2 | 6/2009 | Gong et al. |
| 7,592,418 B2 | 9/2009 | Pathak et al. |
| 8,388,995 B1 | 3/2013 | All et al. |
| 8,765,787 B2 | 7/2014 | Aberg et al. |
| 8,987,339 B2 | 3/2015 | Askari et al. |
| 9,072,809 B2 | 7/2015 | Askari et al. |
| 9,149,560 B2 | 10/2015 | Askari et al. |
| 2001/0003126 A1 | 6/2001 | Rhee et al. |
| 2001/0055615 A1 | 12/2001 | Wallace et al. |
| 2002/0042473 A1 | 4/2002 | Trollsas et al. |
| 2002/0106409 A1 | 8/2002 | Sawhney |
| 2002/0114775 A1 | 8/2002 | Pathak |
| 2002/0165337 A1 | 11/2002 | Wallace et al. |
| 2003/0195113 A1 | 10/2003 | Nakamura et al. |
| 2003/0223957 A1 | 12/2003 | Schwartz et al. |
| 2004/0009205 A1 | 1/2004 | Sawhney |
| 2004/0018228 A1 | 1/2004 | Fischell et al. |
| 2004/0023842 A1 | 2/2004 | Pathak et al. |
| 2004/0033264 A1 | 2/2004 | Sawhney |
| 2004/0191277 A1 * | 9/2004 | Sawhney et al. ............. 424/400 |
| 2004/0203149 A1 | 10/2004 | Childs et al. |
| 2005/0027069 A1 | 2/2005 | Rhee et al. |
| 2005/0200295 A1 | 9/2005 | Lim et al. |
| 2005/0203333 A1 | 9/2005 | Dailey |
| 2005/0208102 A1 | 9/2005 | Schultz |
| 2005/0255039 A1 | 11/2005 | Desai |
| 2005/0281802 A1 | 12/2005 | Gong et al. |
| 2005/0281883 A1 | 12/2005 | Daniloff et al. |
| 2006/0057208 A1 | 3/2006 | Holzer et al. |
| 2006/0065199 A1 | 3/2006 | Davis |
| 2006/0115457 A1 | 6/2006 | Hnojewyj |
| 2006/0147409 A1 | 7/2006 | Pathak et al. |
| 2006/0159771 A1 | 7/2006 | Kadrmas |
| 2006/0222596 A1 | 10/2006 | Askari et al. |

(Continued)

FOREIGN PATENT DOCUMENTS

| CA | 2750242 A1 | 8/2010 |
|---|---|---|
| JP | 2011-505420 A | 2/2011 |

(Continued)

OTHER PUBLICATIONS

Goudar (Therapeutics and Clin Risk Management 4:205-211, 2008).*

(Continued)

*Primary Examiner* — Craig D Ricci
(74) *Attorney, Agent, or Firm* — Pepper Hamilton LLP

(57) ABSTRACT

Provided herein are methods of treating diseases of the lung in a mammal, including cancer of the lung, mesothelioma, emphysema, and bronchopleural fistula. The methods comprise delivering a biocompatible hydrogel polymer optionally comprising a therapeutic agent directly to a target site using a minimally invasive delivery device, wherein the biocompatible hydrogel polymer gels at the target site.

9 Claims, 2 Drawing Sheets

(56) References Cited

U.S. PATENT DOCUMENTS

| | | | |
|---|---|---|---|
| 2007/0110813 | A1 | 5/2007 | Ingenito et al. |
| 2008/0095736 | A1 | 4/2008 | Pathak et al. |
| 2008/0115787 | A1 | 5/2008 | Ingenito |
| 2008/0159975 | A1 | 7/2008 | Nho et al. |
| 2008/0160085 | A1 | 7/2008 | Boland et al. |
| 2008/0214695 | A1 | 9/2008 | Pathak et al. |
| 2008/0261884 | A1* | 10/2008 | Tsai et al. ............... 514/12 |
| 2008/0279944 | A1 | 11/2008 | Sawhney |
| 2008/0281352 | A1 | 11/2008 | Ingenito et al. |
| 2009/0087443 | A1 | 4/2009 | Bartels |
| 2009/0170811 | A1 | 7/2009 | Garvey et al. |
| 2009/0196928 | A1* | 8/2009 | Hnojewyi ............. 424/486 |
| 2009/0215923 | A1 | 8/2009 | Carnahan et al. |
| 2010/0040538 | A1* | 2/2010 | Ingenito ......... A61K 9/007 424/1.25 |
| 2010/0055078 | A1 | 3/2010 | Hughes-Fulford |
| 2010/0113476 | A1 | 5/2010 | Chen et al. |
| 2011/0081701 | A1 | 4/2011 | Sargeant et al. |
| 2011/0091551 | A1 | 4/2011 | Baur et al. |
| 2012/0295869 | A1 | 11/2012 | Liu et al. |
| 2013/0116341 | A1 | 5/2013 | Askari et al. |
| 2014/0248231 | A1 | 9/2014 | Askari et al. |
| 2014/0271528 | A1 | 9/2014 | Askari et al. |
| 2014/0271767 | A1 | 9/2014 | Askari et al. |
| 2014/0302051 | A1 | 10/2014 | Askari et al. |
| 2015/0190544 | A1 | 7/2015 | Askari et al. |
| 2015/0272987 | A1 | 10/2015 | Askari et al. |
| 2015/0273108 | A1 | 10/2015 | Askari et al. |

FOREIGN PATENT DOCUMENTS

| | | | |
|---|---|---|---|
| JP | 201281252 | A | 4/2012 |
| WO | WO-1997-22371 | | 6/1997 |
| WO | WO-1999-003454 | | 1/1999 |
| WO | WO-2001-010416 | | 2/2001 |
| WO | WO-2002-053526 | | 7/2002 |
| WO | WO 02053526 | A1 * | 7/2002 |
| WO | 2002/062276 | A1 | 8/2002 |
| WO | WO-02102864 | A1 | 12/2002 |
| WO | WO-2004-021983 | | 3/2004 |
| WO | WO-2006-030431 | | 3/2006 |
| WO | WO-2007016622 | A2 | 2/2007 |
| WO | WO-2008-141059 | | 11/2008 |
| WO | 2009/073192 | A2 | 6/2009 |
| WO | WO-2009-123768 | | 10/2009 |
| WO | WO-2009-132153 | | 10/2009 |
| WO | WO-2010064251 | A1 | 6/2010 |
| WO | 2010076400 | A8 | 9/2010 |
| WO | WO-2011-057131 | | 5/2011 |
| WO | WO-2011-066291 | | 6/2011 |
| WO | WO-2011-140517 | | 11/2011 |
| WO | WO-2011-140519 | | 11/2011 |
| WO | 2012050591 | A1 | 4/2012 |
| WO | WO-2012057628 | A2 | 5/2012 |

OTHER PUBLICATIONS

3M Company, 3M™ Vetbond™ Veterinary Tissue Adhesive, Material Safety Data Sheet, Jun. 1, 2009.

Abbott Animal Health, GLUture®, Information Brochure, Feb. 2009.

Baino, "Towards an ideal biomaterial for vitreous replacement: Historical overview and future trends," Acta Biomaterialia 7: 921-935 (2011).

Brandi et al., "Biodegradable hydrogels for time-controlled release of tethered peptides or proteins," Biomacromolecules 11: 496-504 (2010).

Campbell et al., "Evaluation of the PleuraSeal™ Lung Sealant System as a Thoracic Sealant in a Canine Lung Resection Model," Covidien (2007).

Creative PEGWorks, Multiarm PEG materials, PEG product Catalog, last updated Dec. 31, 2012.

Dango et al., "Initial experience with a synthetic sealant PleuraSeal™ after pulmonary resections: a prospective study with retrospective case matched controls," Journal of Cardiothoracic Surgery 5: 50-58 (2010).

Ethicon, Inc., Ethicon™ Dermabond Advanced™, Instructions for Use, Status Mar. 2011.

Jemyork Biotechnology, Multiarm PEG materials, web pages printed from www.jemyork.com/proshow.aspx?id=131 on Feb. 12, 2013.

JenKem Technology, USA, Multiarm PEG materials, PEG Products Catalog, 2011.

NanoCS, Inc., Multiarm PEG Derivatives, web pages printed from http://www.nanocs.com/PEG/MAPEG.htm on Feb. 12, 2013.

NeoMend, Inc., ProGEL®, Instructions for Use and Product Labeling, Jan. 4, 2012.

NOF Corporation, Drug Delivery Systems, Catalogue Ver. 13, Prepared Oct. 2011.

Preul et al., "Application of a new hydrogel dural sealant that reduces epidural adhesion formation: evaluation in a large animal laminectomy model," J Neurosurg Spine 12: 381-390 (2010).

International Search Report and Written Opinion for PCT/US2011/035640, dated Jan. 19, 2012.

International Search Report and Written Opinion for PCT/US2011/035643, dated Jan. 19, 2012.

International Search Report for PCT/US2013/40619 dated Sep. 27, 2013.

JenKem Technology USA, "Multi-arm PEG Derivatives," accessed Oct. 7, 2013, http://www.jenkemusa.com/Pages/MultiarmPEGs.aspx.

Lazzarin et al., Efficacy of Enfuvirtide in Patients Infected with Drug-Resistant HIV-1 in Europe and Australia, N. Engl. J. Med., 348(22):2186-2195 (2003).

Marcus et al., The skeletal Response to Teriparatide Is Largely Independent of Age, Initial bone Mineral Density, and Prevalent Vertebral Fractures in Postmenopausal Women With Osteoporisis, J. Bone Miner. Res. 18:18-23 (2003).

Neer et al., Effect of Parathyroid Hormone (1-34) on Fractures and Bone Mineral Density in Postmenopausal Women with Osteoporosis, New Engl. J. Med., 344(19):1434-1441 (2001).

U.S. Appl. No. 13/696,032 Office Action dated Oct. 22, 2013.

PCT/US2014/028622 International Search Report dated Jul. 7, 2014.

U.S. Appl. No. 14/212,457 Office Action dated Jun. 9, 2014.

U.S. Appl. No. 13/696,032 Office Action dated Jun. 12, 2014.

U.S. Appl. No. 14/213,520 Office Action dated Jul. 3, 2014.

Co-pending U.S. Appl. No. 14/618,804, filed Feb. 10, 2015.

PCT/US2014/028798 International Search Report dated Aug. 26, 2014.

U.S. Appl. No. 13/696,032 Office Action dated Dec. 10, 2014.

U.S. Appl. No. 14/213,520 Office Action dated Dec. 15, 2014.

U.S. Appl. No. 14/273,408 Office Action dated Aug. 29, 2014.

U.S. Appl. No. 14/273,408 Office Action dated Nov. 18, 2014.

U.S. Appl. No. 13/571,116 Office Action dated Mar. 4, 2015.

Bailico et al. MultiPEGs: High Molecular Weight Multifunctional Poly(ethylene glycol)s Assembled by a Denrimer-Like Approach. Eur. J. Org. Chem. pp. 2064-2073, (2005).

Co-pending U.S. Appl. No. 14/947,818, filed Nov. 20, 2015.

U.S. Appl. No. 13/571,116 Office Action dated Oct. 22, 2015.

Co-pending U.S. Appl. No. 14/722,829, filed May 27, 2015.

Co-pending U.S. Appl. No. 14/739,917, filed Jun. 15, 2015.

Sardari et al. Evaluation of Clinical Examination for Differential Diagnosis of Lameness by Navicular Apparatus or Heel Pain in Horses. Pakistan Journal of Biological Sciences 11(13):1754-1756 (2008).

U.S. Appl. No. 14/722,829 Office Action dated Aug. 18, 2015.

U.S. Appl. No. 14/739,917 Office Action dated Aug. 4, 2015.

Ostroha. PEG-based Degradable Networks for Drug Delivery Applications. Thesis (165 pgs.) (Jun. 2006).

U.S. Appl. No. 13/571,116 Office Action dated Apr. 27, 2016.

U.S. Appl. No. 13/571,116 Office Action dated Nov. 10, 2016.

U.S. Appl. No. 14/722,829 Office Action dated Aug. 24, 2016.

U.S. Appl. No. 14/722,829 Office Action dated Feb. 5, 2016.

U.S. Appl. No. 14/739,917 Office Action dated Jan. 22, 2016.

U.S. Appl. No. 14/739,917 Office Action dated May 11, 2016.

(56) References Cited

OTHER PUBLICATIONS

U.S. Appl. No. 14/739,917 Office Action dated Nov. 25, 2016.
U.S. Appl. No. 14/947,818 Office Action dated May 9, 2016.
U.S. Appl. No. 14/947,818 Office Action dated Nov. 23, 2016.
U.S. Appl. No. 13/696,032 Office Action dated Jan. 6, 2017.
U.S. Appl. No. 14/947,818 Office Action dated Apr. 16, 2018.
U.S. Appl. No. 15/467,019, Nonfinal Office Action dated Mar. 8, 2018.
EP1317998.3 Search Report dated Feb. 13, 2014.
Nicodemus et al., Cell encapsulation in biodegradable hydrogels for tissue engineering applications, Tissue Engineering Part B 2008 14(2):149-165.
U.S. Appl. No. 13/696,028 Office Action dated Jun. 12, 2014.
U.S. Appl. No. 13/696,032 Office Action dated Jul. 17, 2015.
U.S. Appl. No. 13/696,032 Office Action dated Jun. 8, 2016.
U.S. Appl. No. 14/273,408 Notice of Allowance dated Feb. 10, 2017.
U.S. Appl. No. 14/739,917 Office Action dated Jun. 13, 2017.
U.S. Appl. No. 14/722,829 Notice of Allowance dated Feb. 10, 2017.

\* cited by examiner

METHODS FOR TREATING DISEASES OF THE LUNG

CROSS-REFERENCE

This application is filed pursuant to 35 U.S.C. § 371 as a United States National Phase Application of International Application Ser. No. PCT/US11/035640, filed May 6, 2011, which claims the benefit of U.S. Provisional Application No. 61/387,841, filed Sep. 29, 2010, U.S. Provisional Application No. 61/378,730, filed Aug. 31, 2010, and U.S. Provisional Application No. 61/332,197, filed May 7, 2010, each of which are incorporated herein by reference in their entirety.

BACKGROUND OF THE INVENTION

Every year millions of people undergo systemic treatments, such as chemotherapy for cancers, inflammatory diseases, and chronic conditions. Systemic treatments, in which medications are injected or absorbed into the bloodstream an circulated throughout the body, are currently the only viable option to reach the site of these diseases even though in most cases the disease is localized in a specific organ. However, the systemic approach produces toxic side effects, such as profound nausea and vomiting, immunosuppression and risk or life threatening infections, anemia, hair loss, kidney toxicity, and nerve damage. For many cancer patients the toxicity potential is so severe that chemotherapy cannot be given. In some instances, patients die of the side effects rather than from the cancer.

SUMMARY OF THE INVENTION

Provided herein are methods for treating diseases of the lung. In one aspect, provided herein are methods of treating a cancer of the lung by delivering a biocompatible hydrogel polymer formulation comprising one or more anticancer agents to the site of a lung cancer, e.g., using a bronchoscope or an image guided approach. Further provided herein are methods of treating mesothelioma by delivering the biocompatible hydrogel polymer comprising one or more anticancer agents through the chest cavity to a mesothelioma site using a thoracoscope (or pleurascope) or using an image guided approach. Additionally provided herein are methods of treating bronchopleural fistula by delivering a biocompatible hydrogel polymer to the site of a fistula to seal the fistula. Also provided herein are methods of treating emphysema and COPD by delivering a biocompatible hydrogel polymer to a target site in the lung to controllably collapse a portion of the lung. Using a minimally invasive delivery system (e.g., endoscopic or image guided), the polymeric hydrogel formulation is delivered to the target site in or on the lung, where the in vivo gelling pharmaceutical pre-formulation solidifies at a predetermined time to form a biocompatible hydrogel polymer to remain at the site of delivery. Over time, an optional therapeutic agent (e.g., an anticancer agent) is released from the hydrogel polymer at the target site and is absorbed into the tissue, e.g., inhibiting the growth of a cancer and killing cancer cells, while limiting exposure of healthy cells to the therapeutic agent.

In one aspect provided herein is a method of treating cancer of a lung in a mammal, comprising delivering a biocompatible hydrogel polymer to a target site of the cancer of the lung of the mammal, wherein the biocompatible hydrogel polymer comprises an anticancer agent, and wherein the biocompatible hydrogel polymer gels at the target site of the cancer.

In another aspect provided herein is a method of treating mesothelioma in a mammal, comprising delivering a biocompatible hydrogel polymer to the site of the mesothelioma in the mammal, wherein the biocompatible polymer comprises an anticancer agent, and wherein the biocompatible hydrogel polymer gels at the site of the mesothelioma.

In a further aspect provided herein is a method of treating emphysema in a mammal, comprising delivering a biocompatible hydrogel polymer to a target site in a lung of the mammal affected by the emphysema, wherein the biocompatible hydrogel polymer gels at the target site, wherein the biocompatible hydrogel polymer blocks an air passage or changes the lung surface tension, and wherein a portion of the lung is controllably collapsed.

In an additional aspect provided herein is a method of treating bronchopleural fistula in a mammal, comprising delivering a biocompatible hydrogel polymer to a site of a fistula in a lung of the mammal, wherein the biocompatible hydrogel polymer gels at the site of the fistula, and wherein the biocompatible hydrogel polymer seals the fistula.

In some embodiments of the methods provided herein, the biocompatible hydrogel polymer is delivered via a minimally invasive delivery device. In certain embodiments, the minimally invasive delivery device is an endoscopic device. In some embodiments, the biocompatible hydrogel polymer is delivered to the target site with a bronchoscope. In certain embodiments, the biocompatible hydrogel polymer is delivered to the site of the mesothelioma with a thoracoscope. In some embodiments, the mesothelioma is a pleural mesothelioma. In certain embodiments, the target site is a diseased portion of the lung of the mammal.

In certain embodiments of the methods provided herein, the anticancer agent is selected from the group consisting of docetaxel, paclitaxel, carboplatin, cisplatin, oxaliplatin, satraplatin, etoposide, gemcitabine, or pemetrexed. In some embodiments, the anticancer agent is a toxin. In certain embodiments, the toxin is diphtheria toxin, adenylate cyclase toxin, verotoxin-1, α-toxin, α-hemolysin, curare, or α-cobratoxin. In some embodiments, the anticancer agent is released from the biocompatible hydrogel polymer through diffusion or osmosis. In some embodiments, the biocompatible hydrogel polymer further comprises an additional therapeutic agent. In certain embodiments, the additional therapeutic agent is an anticancer agent, antiviral agent, antibacterial agent, antifungal agent, immunosuppressant agent, or anti-inflammatory agent. In some embodiments, the anticancer agent and/or the additional therapeutic agent is released from the biocompatible hydrogel polymer through diffusion and/or osmosis.

In some embodiments of the methods provided herein, the biocompatible hydrogel polymer comprises a therapeutic agent. In certain embodiments, the therapeutic agent is an anticancer agent, antiviral agent, antibacterial agent, antifungal agent, immunosuppressant agent, or anti-inflammatory agent. In some embodiments, the therapeutic agent is released from the biocompatible hydrogel polymer through diffusion or osmosis.

In certain embodiments of the methods provided herein, the biocompatible hydrogel polymer covers an exposed portion of a tumor at the site of the cancer of the lung of the mammal. In some embodiments, the biocompatible hydrogel polymer adheres to the tumor. In certain embodiments, the biocompatible hydrogel polymer is sprayed onto tissue affected by the mesothelioma. In some embodiments, the biocompatible hydrogel polymer substantially covers tissue affected by the mesothelioma. In certain embodiments, the biocompatible hydrogel polymer adheres to the tissue affected by the mesothelioma. In some embodiments, the biocompatible hydrogel polymer does not significantly cover healthy tissue.

In some embodiments of the methods provided herein, the delivery of the biocompatible hydrogel polymer is guided by imaging technology. In certain embodiments, the imaging technology comprises X-ray, fluoroscopy, computerized tomography, magnetic resonance imaging, ultrasound, positron emission tomography, single photon emission computed tomography, or multimodal imaging methods. In some embodiments, the biocompatible hydrogel polymer further comprises a radiopaque material or a pharmaceutically acceptable dye. In certain embodiments, the radiopaque material is selected from sodium iodide, potassium iodide, barium sulfate, tantalum, VISIPAQUE®, OMNIPAQUE®, or HYPAQUE®, or combinations thereof.

In certain embodiments of the methods provided herein, the biocompatible hydrogel polymer gels at a predetermined time. In some embodiments, the biocompatible hydrogel polymer gels in about 20 seconds to about 5 minutes. In certain embodiments, the biocompatible hydrogel polymer is a bioabsorbable polymer. In some embodiments, the biocompatible hydrogel polymer is bioabsorbed within about 1 to 70 days. In certain embodiments, the biocompatible hydrogel polymer is substantially non-bioabsorbable.

In a further aspect provided herein is a method of treating cancer in a mammal, comprising delivering a mixture of at least one water soluble first compound comprising more than one nucleophilic group, at least one water soluble second compound comprising more than one electrophilic group, an anticancer agent, and an aqueous buffer in the pH range of 5.0 to 9.0, to a site of the cancer, wherein the first compound and the second compound produce a biocompatible hydrogel polymer, wherein the biocompatible hydrogel polymer gels at the site of the cancer, and wherein the biocompatible hydrogel polymer controls the release of the anticancer agent to the site of the cancer.

In some embodiments, the biocompatible hydrogel polymer substantially covers an exposed portion of a tumor at the site of the cancer. In certain embodiments, the biocompatible hydrogel polymer adheres to the tumor. In some embodiments, the biocompatible hydrogel polymer does not significantly cover healthy tissue. In certain embodiments, the mixture further comprises a radiopaque material or a pharmaceutically acceptable dye. In some embodiments, the cancer is lung cancer. In certain embodiments, the mixture is delivered to the site of the cancer with a bronchoscope.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
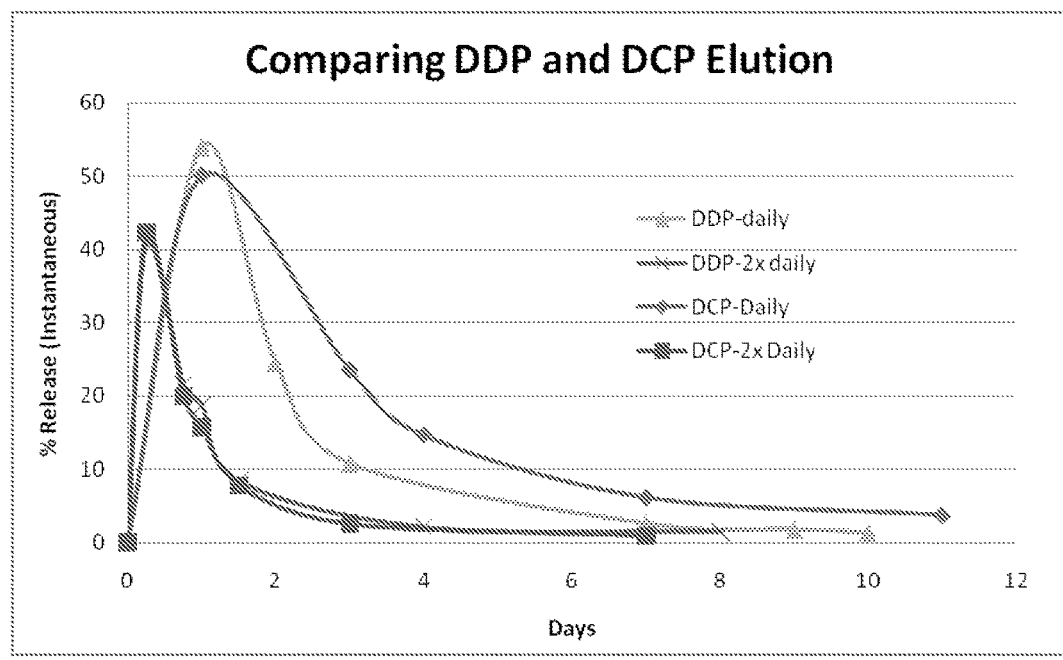
FIG. 1 shows the daily elution of carboplatin (DCP) and cisplatin (DDP) in PBS buffer using one buffer change per day (daily) or two buffer changes per day (2× daily).

Most pharmaceutical therapeutic agents are administered systemically, exposing many cells in the body to the therapeutic agent in addition to the cells at a target site (e.g., in or on a lung). Targeted localized drug delivery directly to a target site limits exposure to the therapeutic agents to the areas surrounding the target site. In certain instances, eliminating the introduction of agents into the systemic blood stream greatly reduces or completely eliminates the side effects associated with systemic treatments and substantially improves the quality of life and life expectancy of patients. In some instances, treatments are more effective because dosages can be increased with less concern for adverse side effects. In further instances, extended release of the therapeutic agent also reduces the number of doses necessary in the course of treatment.

Cancer of the lung is the leading cause of cancer death worldwide. In some instances, the cancer of the lung presents as a tumor accessible from the inside of the lung. In other instances, the cancer of the lung affects the outer tissues and lining of the lung, e.g., in mesothelioma. Furthermore, a potential side effect of surgical removal of a lung tumor is the development of a bronchopleural fistula. Another condition affecting the lung is emphysema and COPD.

An in vivo gelling pre-formulation to form a biocompatible hydrogel polymer enables the administration of medication directly to target sites. The polymer starts out as a liquid pre-formulation and is delivered, with or without one or more optional therapeutic agents, to the site of a disease using minimally invasive techniques. The initial liquid state allows the polymer/drug combination to be delivered through small catheters directed by endoscopes or other image guided techniques to the site of the disease (e.g., bronchoscope for lung, thoracoscope for the chest cavity, laparoscope for the abdominal cavity, cystoscope for the bladder, arthroscope for joint space, etc.). Once in the body, the liquid pre-formulation polymerizes into a solid hydrogel that in some instances adheres to the tissue and keeps the polymer/drug combination at the site of the disease. In some instances, polymerization and degradation times are controlled by varying the composition of the monomers and buffers allowing for the appropriate application and placement of the hydrogel polymer. In some embodiments, the drug is released in a precise and consistent manner. In certain instances, the biocompatible hydrogel polymer is bioabsorbed over a defined period of time. This controlled gelling and biodegradation allows the use of the biocompatible hydrogel polymer to deliver one or more therapeutic agents directly to the tissue affected by a disease, thereby minimizing systemic exposure to the therapeutic agent. Furthermore, the in vivo-gelling pre-formulation allows the placement of the hydrogel at target sites inside a human body to seal a fistula in an internal organ, close passage ways or wounds.

Traditionally, anticancer chemotherapy is administered systemically. Most chemotherapy is delivered intravenously, although a number of agents can be administered orally. In many instances, this approach causes overwhelming systemic damage, because other, normal cells, throughout the body are also damaged by the systemic exposure to the chemotherapeutic agent. Common side effects of cancer treatment are fatigue, pain, nausea, vomiting, decreased blood cell counts, hair loss, and mouth sores. Harmful and lethal toxicity from chemotherapy limits the dosage of chemotherapy that can be given. In certain instances, tumors are destroyed by sufficiently high doses of chemotherapeutic agents. However, in many instances, these high doses cannot be given because they would be fatal to the patient.

In certain instances, local delivery of a therapeutic agent directly to a target using a biocompatible hydrogel polymer achieves the therapeutic effects of the therapeutic agent but without the side effects generally associated with systemic exposure in standard (e.g., oral or parenteral) treatment with the therapeutic agent. In certain embodiments, exposure to the therapeutic agent is limited to the tissue around the target site. In some embodiments, the patient is not exposed systemically to the therapeutic agent. In certain embodiments, a biocompatible hydrogel polymer or in vivo gelling pharmaceutical pre-formulation is used to deliver a therapeutic agent to a target site.

In some instances, the amount of the therapeutic agent, which is delivered to the target site, is increased significantly over standard systemic therapy but with minimal risk of side effects. In some embodiments, the release of therapeutic agents is sustained over longer periods of time than when the therapeutic agent is delivered systemically. In certain embodiments, the local exposure of the tissue at the target site is higher when the therapeutic agent is released from the hydrogel polymer formulation than when the therapeutic agent is delivered systemically. Because the risk of side effects due to the therapeutic agent is reduced, in certain instances, the treatment can be performed in an outpatient department at lower cost than traditional inpatient treatment with systemically delivered chemotherapeutic anticancer agents.

Exemplary Hydrogel Components

Provided herein are in vivo gelling pharmaceutical pre-formulations, comprising at least one water soluble first compound comprising more than one nucleophilic group, at least one water soluble second compound comprising more than one electrophilic group, an aqueous buffer in the pH range of 5.0 to 9.0, and optionally one or more therapeutic agents. In certain embodiments, the in vivo gelling pharmaceutical pre-formulation forms a biocompatible hydrogel polymer at a target site in a human body by mixing the at least one first compound, the at least one second compound, and the optional therapeutic agent in the aqueous buffer and delivering the mixture to the target site such that the biocompatible hydrogel polymer at least in part polymerizes and gels at the target site. In some embodiments, the biocompatible hydrogel polymer is formed following mixing the first compound and the second compound in the aqueous buffer; and wherein the biocompatible hydrogel polymer gels at a target site. In certain embodiments, mixing the first compound, the second compound, and the optional therapeutic agent in the aqueous buffer and delivering the mixture to a target site in the human body generates the in vivo gelling pharmaceutical pre-formulation such that the in vivo gelling pharmaceutical pre-formulation at least in part polymerizes and gels at the target site to form a biocompatible hydrogel polymer.

In some embodiments, the first or second compound comprising more than one nucleophilic or electrophilic group are polyol derivatives. In certain embodiments, the first or second compound is a dendritic polyol derivative. In some embodiments, the first or second compound is a glycol, trimethylolpropane, glycerol, diglycerol, pentaerythritiol, sorbitol, hexaglycerol, tripentaerythritol, or polyglycerol derivative.

In some embodiments, the first and/or second compound further comprises polyethylene glycol (PEG) chains comprising one to 200 ethylene glycol subunits. In certain embodiments, the first and/or second compound further comprises polypropylene glycol (PPG) chains comprising one to 200 propylene glycol subunits.

Exemplary Nucleophilic Monomers

The in vivo gelling pharmaceutical pre-formulation comprises at least one water soluble first compound comprising more than one nucleophilic group. In some embodiments, the nucleophilic group is a hydroxyl, thiol, or amino group. In preferred embodiments, the nucleophilic group is a thiol or amino group.

In certain embodiments, the nucleophilic group is connected to the polyol derivative through a suitable linker. Suitable linkers include, but are not limited to, esters or ethers. In some instances, monomers comprising ester linkers are more susceptible to biodegradation. Examples of linkers comprising a nucleophilic group include, but are not limited to, mercaptoacetate, aminoacetate (glycin) and other amino acid esters (e.g., alanine, β-alanine, lysine, ornithine), 3-mercaptopropionate, ethylamine ether, or propylamine ether. In some embodiments, the polyol core derivative is bound to a polyethylene glycol or polypropylene glycol subunit, which is connected to the linker comprising the nucleophilic group. The molecular weight of the water soluble first compound (the nucleophilic monomer) is about 500 to 40000.

Suitable first compounds comprising a nucleophilic group (used in the amine-ester chemistry) include, but are not limited to, pentaerythritol polyethylene glycol amine (4ARM-PEG-NH2) (molecular weight selected from about 5000 to about 40000, e.g., 5000, 10000, or 20000), pentaerythritol polyethylene glycol amino acetate (4ARM-PEG-AA) (molecular weight selected from about 5000 to about 40000, e.g., 5000, 10000, or 20000), hexaglycerin polyethylene glycol amine (8ARM-PEG-NH2) (molecular weight selected from about 5000 to about 40000, e.g., 10000, 20000, or 40000), or tripentaerythritol glycol amine (8ARM(TP)-PEG-NH2) (molecular weight selected from about 5000 to about 40000, e.g., 10000, 20000, or 40000). Within this class of compounds, 4 (or 8)ARM-PEG-AA comprises ester group while the 4 (or 8)ARM-PEG-NH2 monomers do not comprise ester groups.

Other suitable first compounds comprising a nucleophilic group (used in the thiol-ester chemistry) include, but not limited to, glycol dimercaptoacetate (THIOCURE® GDMA), trimethylolpropane trimercaptoacetate (THIOCURE® TMPMA), pentaerythritol tetramercaptoacetate (THIOCURE® PETMA), glycol di-3-mercaptopropionate (THIOCURE® GDMP), trimethylolpropane tri-3-mercaptopropionate (THIOCURE® TMPMP), pentaerythritol tetra-3-mercaptopropionate (THIOCURE® PETMP), polyol-3-mercaptopropionates, polyester-3-mercaptopropionates, propyleneglycol 3-mercaptopropionate (THIOCURE® PPGMP 800), propyleneglycol 3-mercaptopropionate (THIOCURE® PPGMP 2200), ethoxylated trimethylolpropane tri-3-mercaptopropionate (THIOCURE® ETTMP 700), and ethoxylated trimethylolpropane tri-3-mercaptopropionate (THIOCURE® ETTMP 1300).

Exemplary Electrophilic Monomers

The in vivo gelling pharmaceutical pre-formulation comprises at least one water soluble first compound comprising more than one electrophilic group. In some embodiments, the electrophilic group is an epoxide, maleimide, succinimidyl, or an alpha-beta unsaturated ester. In preferred embodiments, the electrophilic group is an epoxide or succinimidyl.

In certain embodiments, the electrophilic group is connected to the polyol derivative through a suitable linker.

Suitable linkers include, but are not limited to, esters, amides, or ethers. In some instances, monomers comprising ester linkers are more susceptible to biodegradation. Examples of linkers comprising an electrophilic group include, but are not limited to, succinimidyl succinate, succinimidyl glutarate, succinimidyl succinamide, succinimidyl glutaramide, or glycidyl ether. In some embodiments, the polyol core derivative is bound to a polyethylene glycol or polypropylene glycol subunit, which is connected to the linker comprising the electrophilic group. The molecular weight of the water soluble second compound (the electophilic monomer) is about 500 to 40000.

Suitable second compounds comprising an electrophilic group include, but are not limited to, pentaerythritol polyethylene glycol maleimide (4ARM-PEG-MAL) (molecular weight selected from about 5000 to about 40000, e.g., 10000 or 20000), pentaerythritol polyethylene glycol succinimidyl succinate (4ARM-PEG-SS) (molecular weight selected from about 5000 to about 40000, e.g., 10000 or 20000), pentaerythritol polyethylene glycol succinimidyl glutarate (4ARM-PEG-SG) (molecular weight selected from about 5000 to about 40000, e.g., 10000 or 20000), pentaerythritol polyethylene glycol succinimidyl glutaramide (4ARM-PEG-SGA) (molecular weight selected from about 5000 to about 40000, e.g., 10000 or 20000), hexaglycerin polyethylene glycol succinimidyl succinate (8ARM-PEG-SS) (molecular weight selected from about 5000 to about 40000, e.g., 10000 or 20000), hexaglycerin polyethylene glycol succinimidyl glutarate (8ARM-PEG-SG) (molecular weight selected from about 5000 to about 40000, e.g., 10000, 15000, 20000, or 40000), hexaglycerin polyethylene glycol succinimidyl glutaramide (8ARM-PEG-SGA) (molecular weight selected from about 5000 to about 40000, e.g., 10000, 15000, 20000, or 40000), tripentaerythritol polyethylene glycol succinimidyl succinate (8ARM(TP)-PEG-SS) (molecular weight selected from about 5000 to about 40000, e.g., 10000 or 20000), tripentaerythritol polyethylene glycol succinimidyl glutarate (8ARM(TP)-PEG-SG) (molecular weight selected from about 5000 to about 40000, e.g., 10000, 15000, 20000, or 40000), or tripentaerythritol polyethylene glycol succinimidyl glutaramide (8ARM(TP)-PEG-SGA) (molecular weight selected from about 5000 to about 40000, e.g., 10000, 15000, 20000, or 40000). The 4 (or 8)ARM-PEG-SG monomers comprise ester groups, while the 4 (or 8)ARM-PEG-SGA monomers do not comprise ester groups.

Other suitable second compounds comprising an electrophilic group are sorbitol polyglycidyl ethers, including, but not limited to, sorbitol polyglycidyl ether (DENACOL® EX-611), sorbitol polyglycidyl ether (DENACOL® EX-612), sorbitol polyglycidyl ether (DENACOL® EX-614), sorbitol polyglycidyl ether (DENACOL® EX-614 B), polyglycerol polyglycidyl ether (DENACOL® EX-512), polyglycerol polyglycidyl ether (DENACOL® EX-521), diglycerol polyglycidyl ether (DENACOL® EX-421), glycerol polyglycidyl ether (DENACOL® EX-313), glycerol polyglycidyl ether (DENACOL® EX-313), trimethylolpropane polyglycidyl ether (DENACOL® EX-321), sorbitol polyglycidyl ether (DENACOL® EJ-190), Formation of Hydrogels In certain embodiments, the first and second compounds comprising more than one nucleophilic or more than one electrophilic group safely undergo polymerization at a target site inside a mammalian body, for instance on or in an organ, inside a mammalian lung, or inside a joint. In some embodiments, the first compound and the second compound are monomers forming a polymer through the reaction of a nucleophilic group in the first compound with the electrophilic group in the second compound. In certain embodiments, the monomers are polymerized at a predetermined time. In some embodiments, the monomers are polymerized under mild and nearly neutral pH conditions. In certain embodiments, the hydrogel polymer does not change volume after curing.

In some embodiments, one or more first compounds comprising an amino group react with one or more second compounds comprising a succinimidyl ester group to form amide linked first and second monomer units. In certain embodiments, one or more first compounds comprising a thiol group react with one or more second compounds comprising a succinimidyl ester group to form thioester linked first and second monomer units. In some embodiments, one or more first compounds comprising an amino group react with one or more second compounds comprising an epoxide group to from amine linked first and second monomer units. In certain embodiments, one or more first compounds comprising a thiol group react with one or more second compounds comprising an epoxide group to form thioether linked first and second monomer units.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling pharmaceutical pre-formulation. In certain embodiments, temperature influences the gelling time of the in vivo gelling pharmaceutical pre-formulation. In some embodiments, the type of aqueous buffer influences the gelling time of the in vivo gelling pharmaceutical pre-formulation. In certain embodiments, the concentration the aqueous buffer influences the gelling time of the in vivo gelling pharmaceutical pre-formulation. In some embodiments, the nucleophilicity and/or electrophilicity of the nucleophilic and electrophilic groups of the monomers influences the gelling time of the in vivo gelling pharmaceutical pre-formulation.

In certain embodiments, the gelling time or curing time of the biocompatible hydrogel polymer is controlled by the type of aqueous buffer. In some embodiments, the aqueous buffer is a physiologically acceptable buffer. In certain embodiments, aqueous buffers include, but are not limited to, aqueous saline solutions, phosphate buffered saline, borate buffered saline, a combination of borate and phosphate buffers wherein each component is dissolved in separate buffers, N-2-Hydroxyethylpiperazine-N'-2-hydroxypropanesulfonic acid (HEPES), 3-(N-Morpholino) propanesulfonic acid (MOPS), 2-([2-Hydroxy-1,1-bis(hydroxymethyl)ethyl]amino)ethanesulfonic acid (TES), 3-[N-tris(Hydroxy-methyl)ethylamino]-2-hydroxyethyl]-1-piperazinepropanesulfonic acid (EPPS), Tris[hydroxymethyl]-aminomethane (THAM), and Tris[hydroxymethyl]methyl aminomethane (TRIS). In some embodiments, the thiol-ester chemistry (e.g., ETTMP nucleophile with SGA or SG electrophile) is performed in borate buffer. In certain embodiments, the amine-ester chemistry (NH2 or AA nucleophile with SGA or SG electrophile) is performed in phosphate buffer.

In certain embodiments, the first compound and the second compound do not react with the therapeutic agent during formation of the biocompatible hydrogel polymer. In some embodiments, the therapeutic agent remains unchanged after polymerization of the first and second compounds (i.e., monomers). In certain embodiments, the therapeutic agent does not change the properties of the hydrogel polymer. In some embodiments, the physiochemical properties of the therapeutic agent and the hydrogel polymer formulation are not affected by the polymerization of the monomers.

Area of for Treatment—Target Sites

In certain embodiments, the target site is inside a mammal. In some embodiments, the target site is inside a human being. In certain embodiments, the target site is on the human body. In some embodiments, the target site is accessible through surgery. In certain embodiments, the target site is accessible through minimally invasive surgery. In some embodiments, the target site is accessible through an endoscopic device. In certain embodiments, the target site is in or on a lung, in a joint, in the abdomen, in the ovary, bladder, intestine, or blood vessel.

In other embodiments, an in vivo gelling pharmaceutical pre-formulation or a biocompatible hydrogel polymer is used as a sealant or adhesive with or without a therapeutic agent. In certain embodiments, the in vivo gelling pharmaceutical pre-formulation or biocompatible hydrogel polymer is used to seal fistulas in organs inside the human body. In other embodiments, the in vivo gelling pharmaceutical pre-formulation or biocompatible hydrogel polymer is used to fill cavities in the human body.

In some embodiments, the target site is in or on a human lung. In certain embodiments, the target site is a tumor in or on the human lung. In some embodiments, the target site is a tumor of the lung. In certain embodiments, the tumor of the lung is primary or secondary lung cancer. In other embodiments, the cancer of the lung is a cancer on the outside of the lung. In some embodiments, the cancer of the lung affects the pleura. In certain embodiments, the cancer of the lung is a mesothelioma.

In other embodiments, the target site is inside the lung wherein the biocompatible hydrogel polymer functions as a sealant or adhesive. In certain embodiments, the target site inside the lung is a fistula. In some embodiments, the target site is a broncopleural fistula. In certain embodiments, the biocompatible hydrogel polymer is used to seal a fistula. In some embodiments, the in vivo gelling pharmaceutical pre-formulation or biocompatible hydrogel polymer is used to seal off sections of the lung to controllably collapse a portion of the lung.

Target Diseases for Treatment with Biocompatible Hydrogel Polymer

In some embodiments, the biocompatible hydrogel polymer does not comprise a therapeutic agent. In certain embodiments, a biocompatible hydrogel polymer not comprising a therapeutic agent is used in the treatment of fistulas. The in vivo gelling pharmaceutical pre-formulation is delivered to the site of a fistula to seal the fistula by forming a biocompatible hydrogel polymer to cover the hole. In some embodiments, the fistulas that a treated with the biocompatible hydrogel polymer are for example, bronchopleural, enterocutaneous, enterovesicular, or enterovaginal fistulas. In certain embodiments, the in vivo gelling pharmaceutical pre-formulation is delivered through an endoscopic device (e.g., a bronchoscope or thoracoscope). In some embodiments, a biocompatible hydrogel polymer not comprising a therapeutic agent is used in lung volume reduction in the treatment of for example COPD. The in vivo gelling pharmaceutical pre-formulation is delivered to a target site in the lung to controllably collapse a part of the lung. In other embodiments, a biocompatible hydrogel polymer not comprising a therapeutic agent is used as a lubricant for joint disease. In certain embodiments, a biocompatible hydrogel polymer not comprising a therapeutic agent is used to seal wounds.

In certain embodiments, the biocompatible hydrogel polymer comprises a therapeutic agent. In some embodiments, the biocompatible hydrogel polymer comprising a therapeutic agent is used in the treatment of cancers using one or more anticancer agents. In certain embodiments, the cancer is a cancer of the lung (e.g., NSCLC, mesothelioma), ovary, bladder, or colon.

In other embodiments, a biocompatible hydrogel polymer comprising an antifungal therapeutic agent is used in the treatment of aspergillosis and other pulmonary fungal infections. In certain embodiments, a biocompatible hydrogel polymer comprising an antibiotic therapeutic agent is used in the treatment of tuberculosis.

Treatment of Cancer of the Lung

Cancer is a leading cause of death worldwide. Over 7.5 million people die from the various types of cancer every year. Among the most commonly diagnosed cancers are lung and colorectal cancer, with approximately 1.3 million and 0.6 million deaths per year, respectively. Current treatment strategies for many cancers, like lung cancer, are limited to surgical resection for early stage disease and systemic chemotherapy and/or radiation therapy for advanced stage disease. Unfortunately, the majority of patients have advanced stage disease at the time of diagnosis and are not candidates for surgical resection.

Lung cancer is the leading cause of cancer death worldwide. Provided herein are methods of treating a cancer of the lung by delivering a hydrogel polymer formulation containing one or more anticancer agents to the site of the lung cancer, e.g., using a bronchoscope or an image guided approach. Further provided herein are methods of treating mesothelioma by delivering the biocompatible hydrogel polymer through the chest cavity to a mesothelioma site using a thoracoscope (or pleurascope) or using an image guided approach.

Provided herein are compositions comprising and methods of delivering a biocompatible hydrogel polymer containing a therapeutic agent. The compositions and methods are effective and minimally invasive, and provide for local exposure of a cancer to the anticancer drug. In certain embodiments, the compositions comprise a mixture of compounds that safely undergo polymerization to form a biocompatible hydrogel polymer at the site of the cancer. In some instances, the compositions comprise a mixture of compounds that safely undergo polymerization to form a biocompatible hydrogel polymer inside a mammalian lung. The polymeric hydrogel formulation is loaded with a therapeutically effective amount of a therapeutic agent to form a biocompatible hydrogel polymer. Using a minimally invasive technique, the polymeric hydrogel formulation is delivered to the area of the cancer to surround the tumor, where the biocompatible hydrogel polymer solidifies at a predetermined time to remain at the site of delivery. In some embodiments, the biocompatible hydrogel polymer is delivered to the area of the tumor to surround the tumor using an image-guided approach. In certain embodiments, the biocompatible hydrogel polymer is delivered to the area of a tumor inside a mammalian lung to surround the tumor using a bronchoscope. In other instances, the biocompatible hydrogel polymer is delivered to the area of a mesothelioma using an image guided or endoscopic approach, including, but not limited to, thoracoscopy, laparoscopy, or pleurascopy.

In certain embodiments, the biocompatible hydrogel polymer solidifies at a predetermined time to remain at the site of delivery. Over time, the therapeutic agent is released from the biocompatible hydrogel polymer at the site of tumor and is absorbed into the tumor, inhibiting its growth and killing the cancer cells, while limiting exposure of healthy cells to the therapeutic agent. In some embodiments, the biocompatible hydrogel polymer itself is absorbed after a predetermined duration and excreted. In certain instances, the process of delivering the hydrogel polymer containing a chemotherapeutic anticancer drug to the site of the cancer is repeated several times if necessary.

In certain embodiments, the biocompatible hydrogel polymer containing a therapeutic agent is used in the treatment of cancer of the lung. In some embodiments, the cancer is a cancer in the lung. In certain embodiments, the cancer in the lung is a primary lung cancer or a secondary (metastatic) tumor from a non-lung cancer. In some embodiments, an endoscopic delivery device is used to deliver the in vivo gelling pharmaceutical pre-formulation containing a therapeutic agent to the site of the cancer in the lung. In certain embodiments, the mixture is delivered to the site of the tumor in the lung with a bronchoscope. In one embodiment, the in vivo gelling pharmaceutical pre-formulation containing a therapeutic agent is delivered to the site of the tumor through a catheter and deposited onto the tumor. In another embodiment, the in vivo gelling pharmaceutical pre-formulation containing a therapeutic agent is delivered to the site of the tumor through a catheter and sprayed onto the tumor as a thin film using e.g. a nozzle attachment. In some embodiment, the therapeutic agent is a chemotherapeutic agent. In certain embodiments, the chemotherapeutic agent is docetaxel, paclitaxel, carboplatin, cisplatin, oxaliplatin, satraplatin, etoposide, gemcitabine, pemetrexed, or a combination thereof. In other embodiments, the therapeutic agent is a toxin. In certain embodiments, the toxin is diphtheria toxin.

Treatment of Lung Cancer

Provided herein is a method of treating cancer of the lung in a mammal, comprising delivering a mixture of at least one water soluble first compound comprising more than one nucleophilic group, at least one water soluble second compound comprising more than one electrophilic group, an anticancer agent, and an aqueous buffer in the pH range of 5.0 to 9.0, to a site of the cancer; wherein the first compound and the second compound produce a biocompatible hydrogel polymer; wherein the biocompatible hydrogel polymer gels at the site of the cancer; and wherein the biocompatible hydrogel polymer controls the release of the anticancer agent to the site of the cancer. In some embodiments, the cancer is a cancer of the lung. In certain embodiments, the cancer in the lung is a secondary or metastatic tumor from a non-lung cancer. A cancer of the lung includes, but is not limited to, non-small cell lung cancer (NSCLC), squamous cell lung carcinoma, adenocarcinoma, large cell carcinoma, bronchioloalveolar carcinoma, carcinoid tumor, sarcomatoid carcinoma, adenosquamous carcinoma, small cell lung carcinoma (SCLC), pleuropulmonary blastoma, and pulmonary metastases of other cancers (secondary lung tumors).

In some embodiments, a method of treating cancer of a lung in a mammal comprises delivering a biocompatible hydrogel polymer to a target site of the cancer of the lung of the mammal. In certain embodiments, the biocompatible hydrogel polymer comprises an anticancer agent. In some embodiments, the biocompatible hydrogel polymer gels at the target site of the cancer.

In certain embodiments, the biocompatible hydrogel polymer provides structural support to the lung tissue while a tumor of the lung is being destroyed. In some embodiments, the biocompatible hydrogel polymer provides structural strength to keep the bronchi open. In certain embodiments, a biocompatible hydrogel polymer comprising a therapeutic anticancer agent maintains the patency of a bronchos. In other embodiments, a biocompatible hydrogel polymer lacking a therapeutic agent maintains the patency of a bronchos.

In some embodiments, the in vivo gelling pharmaceutical pre-formulation is delivered to the site of a cancer through a catheter or a needle to form a biocompatible hydrogel polymer at the site of the cancer. In certain embodiments, the needle or catheter is attached or part of a delivery device. In some embodiments, the in vivo gelling pharmaceutical pre-formulation containing a therapeutic agent is delivered to the site of a cancer and deposited to cover the tumor. In certain embodiments, the in vivo gelling pharmaceutical pre-formulation containing a therapeutic agent is delivered to the site of the tumor through a catheter and sprayed onto the tumor as a thin film using e.g. a nozzle attachment. In some embodiments, the biocompatible hydrogel polymer is directly injected into the tumor.

In certain embodiments, delivery of the in vivo gelling pharmaceutical pre-formulation to the target site is minimally invasive. In some embodiments, the delivery of the in vivo gelling pharmaceutical pre-formulation to the target site in the body of a subject is image guided, using, for example, X-ray, fluoroscopy, computerized tomography (CT), magnetic resonance imaging (MRI), ultrasound (US), positron emission tomography (PET), single photon emission computed tomography (SPECT), or multimodal imaging methods. In some embodiments, the biocompatible hydrogel polymer formulations further comprise a contrast agent for visualizing the hydrogel formulation and locating a tumor using e.g., X-ray, fluoroscopy, or computed tomography (CT) imaging. In certain embodiments, the contrast agent is radiopaque.

In other embodiments, the in vivo gelling pharmaceutical pre-formulation is delivered to the target site in the body using a catheter attached or integrated into an endoscopic delivery device employing fiber-optics for visualization like, for example, a bronchoscope, pleurascope, or thoracoscope. In certain embodiments, the in vivo gelling pharmaceutical pre-formulation forming a biocompatible hydrogel polymer further comprises a pharmaceutically acceptable dye to enhance visualization using endoscopic delivery techniques. In some embodiments, a delivery device is used to deliver the in vivo gelling pharmaceutical pre-formulation to the site of the cancer. In certain embodiments, the delivery device is an endoscopic device. In some embodiments, the endoscopic device is a bronchoscope. In certain embodiments, the bronchoscope is navigated to a tumor location in the lung of a mammal. In some embodiments, the in vivo gelling pharmaceutical pre-formulation containing the therapeutic agent is delivered through a catheter attached to the bronchoscope or other endoscopic delivery device. In some embodiments, the catheter has an outer diameter of about 4 mm, about 3.8 mm, about 3.6 mm, about 3.4 mm, about 3.2 mm, about 3.0 mm, about 2.8 mm, about 2.6 mm, about 2.4 mm, about 2.2 mm, about 2.0 mm, about 1.8 mm, about 1.6 mm, about 1.4 mm, about 1.2 mm, about 1.0 mm, about 0.8 mm, or about 0.6 mm. In preferred embodiments, the catheter has an outer diameter of about 1.2 mm. In certain embodiments, the viscosity of the in vivo gelling pharmaceutical pre-formulation is close to the viscosity of water when delivering the mixture to the site of the tumor through the catheter.

In certain embodiments, between 10 and 30 mL of the in vivo gelling pharmaceutical pre-formulation containing the therapeutic agent is delivered to the site of a tumor. In some embodiments, the gelling time of the biocompatible hydrogel polymer is set according to the preference of the doctor delivering the hydrogel polymer mixture to the site of the cancer. In most instances, a physician delivers the hydrogel polymer mixture to the site of the cancer within 15 to 30 seconds. In some embodiments, the hydrogel polymer mixture gels after delivery at the site of the cancer, covering the tumor.

In some embodiments, the gelling time or curing time of the biocompatible hydrogel polymer is controlled by the pH of the aqueous buffer. In certain embodiments, the gelling time is between about 20 seconds and 5 minutes. In preferred embodiments, the gelling time is about 90 seconds. In certain embodiments, the pH of the aqueous buffer is from about 5 to about 9. In some embodiments, the pH of the aqueous buffer is from about 6.9 to about 7.9. In specific embodiments, the pH of the aqueous buffer is about 7.4. In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling pharmaceutical pre-formulation.

In some embodiments, the in vivo gelling pharmaceutical pre-formulation containing the therapeutic agent is delivered to the tumor location so that the mixture loaded with the therapeutic agent mostly covers the tumor. In certain embodiments, the in vivo gelling pharmaceutical pre-formulation substantially covers an exposed portion of the tumor. In some embodiments, the in vivo gelling pharmaceutical pre-formulation containing the therapeutic agent does not spread to any other location intentionally. In some embodiments, the in vivo gelling pharmaceutical pre-formulation containing the therapeutic agent substantially covers a tumor and does not significantly cover healthy tissue. In certain embodiments, the biocompatible hydrogel polymer does not significantly cover healthy tissue. In some embodiments, the mixture of monomers loaded with the therapeutic agent gels over the tumor and thoroughly covers the tumor. In some embodiments, the biocompatible hydrogel polymer adheres to the tumor.

In some embodiments, the biocompatible hydrogel polymer slowly delivers the drug to the tumor by diffusion and/or osmosis over time ranging from hours to days. In other embodiments, the drug is released from the biocompatible hydrogel polymer during the biodegradation of the hydrogel. In certain embodiments, the drug is delivered directly to the tumor. Over time the drug stops the tumor growth; the tumor shrinks and slowly disappears. In some embodiments, the procedure of delivering a biocompatible hydrogel polymer containing an anticancer agent to the site of the cancer is repeated for the same tumor several times, if needed. In certain embodiments, the therapeutic anticancer agent is substantially released from the biocompatible hydrogel polymer within about 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, about 1 day, about 0.5 day, about 6 hours, about 4 hours, about 2 hours, about or 1 hour. In some embodiments, the therapeutic anticancer agent is substantially released from the biocompatible hydrogel polymer within more than 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, more than 1 day, more than 0.5 day, more than 6 hours, more than 4 hours, more than 2 hours, more than or 1 hour. In certain embodiments, the therapeutic anticancer agent is substantially released from the biocompatible hydrogel polymer within less than 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, less than 1 day, less than 0.5 day, less than 6 hours, less than 4 hours, less than 2 hours, less than or 1 hour. In some embodiments, the therapeutic anticancer agent is substantially released from the biocompatible hydrogel polymer within about one day to about fourteen days. In certain embodiments, the therapeutic anticancer agent is substantially released from the biocompatible hydrogel polymer within about one day to about 70 days.

In some embodiments, the biocompatible hydrogel polymer is a bioabsorbable polymer. In certain embodiments, the biocompatible hydrogel polymer is bioabsorbed within about 5 to 30 days. In some embodiments, the biocompatible hydrogel polymer is bioabsorbed within about 30 to 180 days. In preferred embodiments, the biocompatible hydrogel polymer is bioabsorbed within about 1 to 70 days. In some embodiments the biocompatible hydrogel polymer is bioabsorbed within about 365 days, 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, or about 1 day. In certain embodiments the biocompatible hydrogel polymer is bioabsorbed within less than 365 days, 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, or less than 1 day. In some embodiments the biocompatible hydrogel polymer is bioabsorbed within more than 365 days, 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, or more than 1 day. In some embodiments, the biocompatible hydrogel polymer is substantially non-bioabsorbable.

The biocompatible hydrogel polymer is slowly bioabsorbed, dissolved, and or excreted. In some instances, the rate of bioabsorption can be controlled by the number of ester groups in the biocompatible and/or biodegradable hydrogel polymer. In other instances, the higher the concentration of ester units is in the biocompatible hydrogel polymer, the longer is its lifetime in the body. In further instances, the electron density at the carbonyl of the ester unit controls the lifetime of the hydrogel polymer in the body. In certain instances, biocompatible hydrogel polymers without ester groups are essentially not biodegradable. In additional instances, the molecular weight of the first and second compounds controls the lifetime of the hydrogel polymer in the body. In further instances, the number of ester groups per gram of polymer controls the lifetime of the hydrogel polymer in the body.

In some instances, the lifetime of the hydrogel polymer can be estimated using a model, which controls the temperature and pH at physiological levels while exposing the hydrogel polymer to a buffer solution. In certain instances, the biodegradation of the hydrogel polymer is substantially non-enzymatic degradation.

Treatment of Mesothelioma

Provided herein is a method of treating mesothelioma in a mammal, comprising delivering a mixture of at least one water soluble first compound comprising more than one nucleophilic group, at least one a water soluble second compound comprising more than one electrophilic group, an anticancer agent, and an aqueous buffer in the pH range of 5.0 to 9.0, to a site of the mesothelioma, wherein the first compound and the second compound produce a biocompatible hydrogel polymer; wherein the biocompatible hydrogel polymer gels at the site of the mesothelioma; and wherein the biocompatible hydrogel polymer controls the release of the anticancer agent to the site of the mesothelioma.

In some embodiments, the biocompatible hydrogel polymer containing a therapeutic agent is used in the treatment of mesothelioma. In certain embodiments, an endoscopic delivery device is used to deliver the in vivo gelling pharmaceutical pre-formulation containing a therapeutic agent to the site of the mesothelioma. In some embodiments, the mixture is delivered to the site of the tumor in the thoracic (chest) cavity with a pleurascope. In other embodiments, the mixture is delivered to the site of the mesothelioma with a thoracoscope. In some embodiments, the in vivo gelling pharmaceutical pre-formulation containing a therapeutic agent is delivered to the site of a cancer and deposited to cover the tumor. In certain instances, the mesothelioma is spread diffusely throughout the affected tissues. In one embodiment, the in vivo gelling pharmaceutical pre-formulation containing a chemotherapeutic anticancer agent is delivered to the tissues affected by mesothelioma through a catheter and sprayed onto the tissues affected by mesothelioma as a thin film using e.g. a nozzle attachment. In some embodiments, the sprayed on biocompatible hydrogel polymer covers the tissues affected by the mesothelioma and the hydrogel polymer releases the therapeutic agent over a period of time. In some embodiment, the therapeutic agent is a chemotherapeutic anticancer agent. In certain embodiments, the therapeutic agent is docetaxel, paclitaxel, carboplatin, cisplatin, oxaliplatin, satraplatin, etoposide, gemcitabine, pemetrexed, or a combination thereof. In other embodiments, the therapeutic agent is a toxin. In certain embodiments, the toxin is diphtheria toxin.

In some embodiments, a method of treating mesothelioma in a mammal comprises delivering a biocompatible hydrogel polymer to the site of the mesothelioma in the mammal. In some embodiments, the biocompatible hydrogel polymer comprises an anticancer agent. In certain embodiments, the biocompatible hydrogel polymer gels at the site of the mesothelioma.

In certain embodiments, the biocompatible hydrogel polymer provides structural support to the lung tissue while a tumor of the lung is being destroyed.

In some embodiments, the in vivo gelling pharmaceutical pre-formulation is delivered to the site of a mesothelioma through a catheter or a needle to form a biocompatible hydrogel polymer at the site of the mesothelioma. In certain embodiments, the needle or catheter is attached or part of a delivery device. In some embodiments, the in vivo gelling pharmaceutical pre-formulation containing a therapeutic anticancer agent is delivered to the site of a mesothelioma and deposited to cover the tumor. In certain embodiments, the in vivo gelling pharmaceutical pre-formulation containing a chemotherapeutic anticancer agent is delivered to the site of the tumor through a catheter and sprayed onto the tumor as a thin film using e.g. a nozzle attachment. In some embodiments, the biocompatible hydrogel polymer is directly injected into the tumor.

In certain embodiments, delivery of the in vivo gelling pharmaceutical pre-formulation to the target site is minimally invasive. In some embodiments, the delivery of the in vivo gelling pharmaceutical pre-formulation to the target site in the body of a subject is image guided, using, for example, X-ray, fluoroscopy, computerized tomography (CT), magnetic resonance imaging (MRI), ultrasound (US), positron emission tomography (PET), single photon emission computed tomography (SPECT), or multimodal imaging methods. In some embodiments, the biocompatible hydrogel polymer formulations further comprise a contrast agent for visualizing the hydrogel formulation and locating a tumor using e.g., X-ray, fluoroscopy, or computed tomography (CT) imaging. In certain embodiments, the contrast agent is radiopaque.

In other embodiments, the in vivo gelling pharmaceutical pre-formulation is delivered to the target site in the body using a catheter attached or integrated into an endoscopic delivery device employing fiber-optics for visualization like, for example, a bronchoscope, pleurascope, or thoracoscope. In certain embodiments, the in vivo gelling pharmaceutical pre-formulation forming a biocompatible hydrogel polymer further comprises a pharmaceutically acceptable dye to enhance visualization using endoscopic delivery techniques. In some embodiments, a delivery device is used to deliver the in vivo gelling pharmaceutical pre-formulation to the site of the mesothelioma. In certain embodiments, the delivery device is an endoscopic device. In some embodiments, the endoscopic device is a pleurascope. In certain embodiments, the pleurascope is navigated to a tumor location on the lung of a mammal. In some embodiments, the in vivo gelling pharmaceutical pre-formulation containing the therapeutic agent is delivered through a catheter attached to the pleurascope or other endoscopic delivery device. In some embodiments, the catheter has an outer diameter of about 4 mm, about 3.8 mm, about 3.6 mm, about 3.4 mm, about 3.2 mm, about 3.0 mm, about 2.8 mm, about 2.6 mm, about 2.4 mm, about 2.2 mm, about 2.0 mm, about 1.8 mm, about 1.6 mm, about 1.4 mm, about 1.2 mm, about 1.0 mm, about 0.8 mm, or about 0.6 mm. In preferred embodiments, the catheter has an outer diameter of about 1.2 mm. In certain embodiments, the viscosity of the in vivo gelling pharmaceutical pre-formulation is close to the viscosity of water when delivering the mixture to the site of the tumor through the catheter.

In certain embodiments, between 10 and 100 mL of the in vivo gelling pharmaceutical pre-formulation containing the therapeutic agent is delivered to the site of a tumor. In some embodiments, the gelling time of the biocompatible hydrogel polymer is set according to the preference of the doctor delivering the hydrogel polymer mixture to the site of the mesothelioma. In most instances, a physician delivers the hydrogel polymer mixture to the site of the mesothelioma within 15 to 30 seconds. In some embodiments, the hydrogel polymer mixture gels after delivery at the site of the mesothelioma, covering the tumor.

In some embodiments, the gelling time or curing time of the biocompatible hydrogel polymer is controlled by the pH of the aqueous buffer. In certain embodiments, the gelling time is between about 20 seconds and 5 minutes. In preferred embodiments, the gelling time is about 90 seconds. In certain embodiments, the pH of the aqueous buffer is from about 5 to about 9. In some embodiments, the pH of the aqueous buffer is from about 6.9 to about 7.9. In specific embodiments, the pH of the aqueous buffer is about 7.4. In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the in vivo gelling pharmaceutical pre-formulation.

In some embodiments, the in vivo gelling pharmaceutical pre-formulation containing the therapeutic agent is delivered to the tumor location so that the mixture loaded with the therapeutic agent mostly covers the tumor. In certain embodiments, the in vivo gelling pharmaceutical pre-formulation substantially covers an exposed portion of the tumor. In some embodiments, the in vivo gelling pharmaceutical pre-formulation containing the therapeutic agent does not spread to any other location intentionally. In some embodiments, the in vivo gelling pharmaceutical pre-formulation containing the therapeutic agent substantially covers a tumor and does not significantly cover healthy tissue. In certain embodiments, the biocompatible hydrogel polymer does not significantly cover healthy tissue. In some embodiments, the mixture of monomers loaded with the therapeutic agent gels over the tumor and thoroughly covers the tumor. In some embodiments, the biocompatible hydrogel polymer adheres to the tumor.

In some embodiments, the biocompatible hydrogel polymer slowly delivers the drug to the tumor by diffusion and/or osmosis over time ranging from hours to days. In other embodiments, the drug is released from the biocompatible hydrogel polymer during the biodegradation of the hydrogel. In certain embodiments, the drug is delivered directly to the tumor. Over time the drug stops the tumor growth; the tumor shrinks and slowly disappears. In some embodiments, the procedure of delivering a biocompatible hydrogel polymer containing an anticancer agent to the site of the mesothelioma is repeated for the same tumor several times, if needed. In certain embodiments, the therapeutic anticancer agent is substantially released from the biocompatible hydrogel polymer within about 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, about 1 day, about 0.5 day, about 6 hours, about 4 hours, about 2 hours, about or 1 hour. In some embodiments, the therapeutic anticancer agent is substantially released from the biocompatible hydrogel polymer within more than 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, more than 1 day, more than 0.5 day, more than 6 hours, more than 4 hours, more than 2 hours, more than or 1 hour. In certain embodiments, the therapeutic anticancer agent is substantially released from the biocompatible hydrogel polymer within less than 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, less than 1 day, less than 0.5 day, less than 6 hours, less than 4 hours, less than 2 hours, less than or 1 hour. In some embodiments, the therapeutic anticancer agent is substantially released from the biocompatible hydrogel polymer within about one day to about fourteen days. In certain embodiments, the therapeutic anticancer agent is substantially released from the biocompatible hydrogel polymer within about one day to about 70 days.

In some embodiments, the biocompatible hydrogel polymer is a bioabsorbable polymer. In certain embodiments, the biocompatible hydrogel polymer is bioabsorbed within about 5 to 30 days. In some embodiments, the biocompatible hydrogel polymer is bioabsorbed within about 30 to 180 days. In preferred embodiments, the biocompatible hydrogel polymer is bioabsorbed within about 1 to 70 days. In some embodiments the biocompatible hydrogel polymer is bioabsorbed within about 365 days, 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, or about 1 day. In certain embodiments the biocompatible hydrogel polymer is bioabsorbed within less than 365 days, 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, or less than 1 day. In some embodiments the biocompatible hydrogel polymer is bioabsorbed within more than 365 days, 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, or more than 1 day. In some embodiments, the biocompatible hydrogel polymer is substantially non-bioabsorbable.

The biocompatible hydrogel polymer is slowly bioabsorbed, dissolved, and or excreted. In some instances, the rate of bioabsorption can be controlled by the number of ester groups in the biocompatible and/or biodegradable hydrogel polymer. In other instances, the higher the concentration of ester units is in the biocompatible hydrogel polymer, the longer is its lifetime in the body. In further instances, the electron density at the carbonyl of the ester unit controls the lifetime of the hydrogel polymer in the body. In certain instances, biocompatible hydrogel polymers without ester groups are essentially not biodegradable. In additional instances, the molecular weight of the first and second compounds controls the lifetime of the hydrogel polymer in the body. In further instances, the number of ester groups per gram of polymer controls the lifetime of the hydrogel polymer in the body.

In some instances, the lifetime of the hydrogel polymer can be estimated using a model which controls the temperature and pH at physiological levels while exposing the hydrogel polymer to a buffer solution. In certain instances, the biodegradation of the hydrogel polymer is substantially non-enzymatic degradation.

Exemplary Anticancer Agents

In some embodiments, the anticancer agent is a chemotherapeutic anticancer agent. In certain embodiments, the biocompatible hydrogel polymer is loaded with a desired amount of one or more chemotherapeutic anticancer agents to form a biocompatible hydrogel polymer. Examples of chemotherapeutic anticancer agents include Nitrogen Mustards like bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides like etoglucid; Other Alkylating Agents like dacarbazine, mitobronitol, pipobroman, temozolomide; Folic Acid Analogues like methotrexate, permetrexed, pralatrexate, raltitrexed; Purine Analogs like cladribine, clofarabine, fludarabine, mercaptopurine, nelarabine, tioguanine; Pyrimidine Analogs like azacitidine, capecitabine, carmofur, cytarabine, decitabine, fluorouracil, gemcitabine, tegafur; Vinca Alkaloids like vinblastine, vincristine, vindesine, vinflunine, vinorelbine; Podophyllotoxin Derivatives like etoposide, teniposide; Colchicine derivatives like demecolcine; Taxanes like docetaxel, paclitaxel, paclitaxel poliglumex; Other Plant Alkaloids and Natural Products like trabectedin; Actinomycines like dactinomycin; Antracyclines like aclarubicin, daunorubicin, doxorubicin, epirubicin, idarubicin, mitoxantrone, pirarubicin, valrubicin, zorubincin; Other Cytotoxic Antibiotics like bleomycin, ixabepilone, mitomycin, plicamycin; Platinum Compounds like carboplatin, cisplatin, oxaliplatin, satraplatin; Methylhydrazines like procarbazine; Sensitizers like aminolevulinic acid, efaproxiral, methyl aminolevulinate, porfimer sodium, temoporfin; Protein Kinase Inhibitors like dasatinib, erlotinib, everolimus, gefitinib, imatinib, lapatinib, nilotinib, pazonanib, sorafenib, sunitinib, temsirolimus; Other Antineoplastic Agents like alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens like diethylstilbenol, ethinylestradiol, fosfestrol, polyestradiol phosphate; Progestogens like gestonorone, medroxyprogesterone, megestrol; Gonadotropin Releasing Hormone Analogs like buserelin, goserelin, leuprorelin, triptorelin; Anti-Estrogens like fulvestrant, tamoxifen, toremifene; Anti-Androgens like bicalutamide, flutamide, nilutamide; Enzyme Inhibitors like aminoglutethimide, anastrozole, exemestane, formestane, letrozole, vorozole; Other Hormone Antagonists like abarelix, degarelix; Immunostimulants like histamine dihydrochloride, mifamurtide, pidotimod, plerixafor, roquinimex, thymopentin; Immunosuppressants like everolimus, gusperimus, leflunomide, mycophenolic acid, sirolimus; Calcineurin Inhibitors like ciclosporin, tacrolimus; Other Immunosuppressants like azathioprine, lenalidomide, methotrexate, thalidomide; and Radiopharmaceuticals like iobenguane.

In preferred embodiments, the chemotherapeutic anticancer agent is selected from, but not limited to, docetaxel, paclitaxel, paclitaxel poliglumex, ixabepilone, carboplatin, cisplatin, oxaliplatin, satraplatin, gemcitabine, etoposide, or pemetrexed.

In some embodiments, the anticancer agent is a toxin, e.g. diphtheria toxin. In certain embodiments, the biocompatible hydrogel polymer is loaded with a therapeutically effective amount of one or more toxins to form a biocompatible hydrogel polymer. Examples of toxins include Exotoxins like diphtheria toxin, botulinium toxin, cytolysins, hemolysins (e.g., α-toxin or α-hemolysin of *Staphyllococcus aureus*), cholera toxin, pertussis toxin, Shiga toxin; Heat-Stable Enterotoxin from *E. coli*; Curare; α-Cobratoxin; Verotoxin-1; and Adenylate Cyclase (AC) toxin from *Bordetella pertussis*.

Because the anticancer agent is administered locally and directly to the tumor tissue, the anticancer agent is delivered to only a small part of the body of the patient. Therefore, the total dose delivered to a patient using the biocompatible hydrogel polymer formulation is lower than the total dose using systemic administration. However, the dose delivered to the tumor using the biocompatible hydrogel polymer formulation can be larger than the dose that reaches the tumor site when the anticancer agent is delivered systemically.

For instance, the dose of cisplatin for a normal human (body surface area 1.73 $m^2$) is about 173 mg (at 100 $mg/m^2$) administered systemically. The maximum dose of cisplatin using the biocompatible hydrogel polymer formulation can be up to 120 mg directly to the site of the tumor (solubility of cisplatin is 1 mg/mL and up to 120 mL of hydrogel can be safely delivered).

In some embodiments, the amount of the anticancer agent delivered to the site of a cancer in a biocompatible hydrogel polymer formulation is about 1000 mg, about 900 mg, about 800 mg, about 700 mg, about 600 mg, about 500 mg, about 400 mg, about 300 mg, about 250 mg, about 200 mg, about 150 mg, about 100 mg, about 90 mg, about 80 mg, about 70 mg, about 60 mg, about 50 mg, about 40 mg, about 30 mg, about 28 mg, about 26 mg, about 25 mg, about 24 mg, about 22 mg, about 20 mg, about 18 mg, about 16 mg, about 15 mg, about 14 mg, about 12 mg, about 10 mg, about 9 mg, about 8 mg, about 7 mg, about 6 mg, about 5 mg, about 4 mg, about 3 mg, about 2 mg, or about 1 mg.

Treatment Alternative to Lung Volume Reduction Surgery (LVRS)

In some embodiments, the biocompatible hydrogel polymer is used in the treatment of emphysema as an alternative to lung volume reduction surgery (LVRS). LVRS is carried out by surgically removing up to a 20-30% portion of the diseased lung. LVRS is considered one of the riskiest elective procedures. In one alternative to LVRS, a mechanical device is focused on providing a clear oxygen/air passage for the lung either by installing one-way valves or by creating permanent openings in the lung. In another alternative to LVRS, a portion of the lung or the entire lung is controllably collapsed either by blocking the air passage and/or changing the lung surface tension using adhesives. Additionally, in certain instances, an exothermic source, generally steam, is used to heat and collapse the lung.

Provided herein are in vivo gelling pharmaceutical pre-formulations, comprising at least one water soluble first compound comprising more than one nucleophilic group, at least one water soluble second compound comprising more than one electrophilic group, and an aqueous buffer in the pH range of 5.0 to 9.0, wherein a biocompatible hydrogel polymer is formed following mixing the first compound and the second compound in the aqueous buffer, wherein the biocompatible hydrogel polymer gels at a target site. In some embodiments, the target site is a diseased portion of a mammalian lung.

Also provided herein are methods of preparing a diseased region of a lung for volume reduction, the method comprising introducing a biocompatible hydrogel polymer formulation into a diseased region of a lung to reduce the volume of that region, wherein the material is introduced via a minimally invasive delivery system, and wherein the biocompatible hydrogel polymer formulation comprises a combination of two or more biocompatible monomers. Further provided herein is a minimally invasive treatment for lung disease such as emphysema, wherein a biocompatible hydrogel polymer is delivered to the target site in the lung using a minimally invasive delivery device like a bronchoscope, and wherein a portion of the lung is controllably collapsed by blocking the air passage or by changing the lung surface tension.

In certain embodiments, the biocompatible hydrogel polymer is used to control the collapse of a diseased portion of the lung. In some embodiments, the biocompatible hydrogel polymer formulation used in the treatment of emphysema does not comprise a therapeutic agent. In certain embodiments, the biocompatible hydrogel polymer optionally comprises a therapeutic agent. In some embodiments, the biocompatible hydrogel polymer does not stick to the tip of a delivery system. In certain embodiments, the biocompatible hydrogel polymer prevents a delivery tube from sticking to the target site in the lung. In some embodiments, the biocompatible hydrogel polymer does not contain biological materials like fibrin and does not pose a risk of allergic reactions.

In certain embodiments, a first and second compound comprising at least one nucleophilic or at least one electrophilic group safely undergo polymerization at a target site inside a mammalian body cavity, for instance inside a mammalian lung. In some embodiments, the first compound and second compound are water soluble and form a hydrogel upon polymerization. In certain embodiments, the monomers are polymerized at a predetermined time. In certain embodiments, the hydrogel polymer does not change volume after curing.

In some embodiments, the biocompatible hydrogel polymer is formed at or near the location of the diseased tissue. In certain embodiments, the monomers are injected inside the lung through bronchi and bronchioles using a catheter and a minimally invasive delivery system. In some embodiments, the delivery system is a bronchoscope. In certain embodiments, the monomers fill the diseased cavity and the bronchi and bronchioles passage to the diseased portion of the lung before gelling. In some embodiments, the polymers stay at the location and do not flow outside the target area.

In certain embodiments, the formation of the hydrogel polymer generates a controlled heat. In some embodiments, the heat generated at the target site is controlled by optionally formulating the hydrogel polymer monomers with highly viscous materials, wherein the highly viscous materials act as heat sinks in the formulation.

In some embodiments, the polymer formation and/or gelling takes place inside the human body at the target site. In certain embodiments, the monomers are mixed prior to delivery to control the state of the reaction prior to delivery to the target site. In some embodiment, the polymer is injected inside the body at the target site before the gel time/cure time of the hydrogel polymer mixture. In certain embodiments, the in vivo gelling pharmaceutical pre-formulation optionally comprises a material with a radiopaque or other desired property within the material in order to monitor the progress of filling the lung cavity or other physical characteristic of the state of the body or the procedure.

In certain embodiments, the biocompatible hydrogel polymers are polymerized in situ in a mammalian cavity. In some embodiments, the polymerization takes place instantly after delivering the polymer to the target cavity. In other embodiments, the reaction takes place after a longer period of time.

Treatment of Bronchopleural Fistula

In some embodiments, the biocompatible hydrogel polymer is used in the treatment of bronchopleural fistula. A bronchopleural fistula is a fistula (hole) located between the pleural space and the lung. Provided here is a method of treating bronchopleural fistula in a mammal, comprising delivering a biocompatible hydrogel polymer to a site of a fistula in a lung of the mammal. In some embodiments, the biocompatible hydrogel polymer gels at the site of the fistula. In certain embodiments, the biocompatible hydrogel polymer seals the fistula. In some embodiments, incorporation of antibiotics and anti-inflammatory agents is useful for fistula repair.

In some embodiments, the biocompatible hydrogel polymer used in the treatment of bronchopleural fistula does not comprise a therapeutic agent. In certain embodiments, the biocompatible hydrogel polymer optionally comprises a therapeutic agent. In some embodiments, the biocompatible hydrogel polymer does not stick to the tip of a delivery system. In certain embodiments, the biocompatible hydrogel polymer prevents a delivery tube from sticking to the target site in the lung. In some embodiments, the biocompatible hydrogel polymer does not contain biological materials like fibrin and does not pose a risk of allergic reactions.

In certain embodiments, a first and second compound comprising at least one nucleophilic or at least one electrophilic group safely undergo polymerization at a target site inside a mammalian body cavity, for instance inside a mammalian lung. In some embodiments, the first compound and second compound are water soluble and form a hydrogel upon polymerization. In certain embodiments, the monomers are polymerized at a predetermined time. In certain embodiments, the hydrogel polymer does not change volume after curing.

In some embodiments, the biocompatible hydrogel polymer is formed at or near the location of the damaged tissue. In certain embodiments, the monomers are injected inside the lung through bronchi and bronchioles using a catheter and a minimally invasive delivery system. In some embodiments, the delivery system is a bronchoscope. In certain embodiments, the monomers seal the damaged portion of the lung before gelling. In some embodiments, the polymers stay at the location and do not flow outside the target area.

In certain embodiments, the formation of the hydrogel polymer generates a controlled heat. In some embodiments, the heat generated at the target site is controlled by optionally formulating the hydrogel polymer monomers with highly viscous materials, wherein the highly viscous materials act as heat sinks in the formulation.

In some embodiments, the polymer formation and/or gelling takes place inside the human body at the target site. In certain embodiments, the monomers are mixed prior to delivery to control the state of the reaction prior to delivery to the target site. In some embodiment, the polymer is injected inside the body at the target site before the gel time/cure time of the hydrogel polymer mixture. In certain embodiments, the in vivo gelling pharmaceutical pre-formulation optionally comprises a material with a radiopaque or other desired property within the material in order to monitor the progress of sealing the fistula. In some embodiments, the radiopaque material assists in determining the bioabsorption of the biocompatible hydrogel polymer.

In certain embodiments, the in vivo gelling pharmaceutical pre-formulation forming a biocompatible hydrogel polymer is polymerized in situ in a mammalian cavity. In some embodiments, the polymerization takes place instantly after delivering the polymer to the target cavity. In other embodiments, the reaction takes place after a longer period of time.

Exemplary Combinations

In some embodiments, a second anticancer agent can be incorporated into the biocompatible hydrogel polymer formulation. Provided herein are in vivo gelling pharmaceutical pre-formulations, comprising a water soluble first compound comprising more than one nucleophilic group, a water soluble second compound comprising more than one electrophilic group, a first anticancer agent, a second anticancer agent, and an aqueous buffer in the pH range of 5.0 to 9.0, wherein a biocompatible hydrogel polymer is formed following mixing the first compound and the second compound in the aqueous buffer; and wherein the biocompatible hydrogel polymer gels at a site of a cancer. In some embodiments, the first compound and the second compound do not react with the first and second anticancer agent during formation of the biocompatible hydrogel polymer. In preferred embodiments, the second anticancer agent is selected from, but not limited to, docetaxel, paclitaxel, paclitaxel poliglumex, ixabepilone, carboplatin, cisplatin, oxaliplatin, satraplatin, etoposide, gemcitabine, or pemetrexed.

In certain embodiments, the biocompatible hydrogel polymer comprises two or more anticancer agents. In some embodiments, the anticancer agents are chemotherapeutic anticancer agents. In preferred embodiments, the anticancer agents are selected from but not limited to, docetaxel, paclitaxel, paclitaxel poliglumex, ixabepilone, carboplatin, cisplatin, oxaliplatin, satraplatin, etoposide, gemcitabine, or pemetrexed.

In certain embodiments, the in vivo gelling pharmaceutical pre-formulations comprise additional therapeutic agents. Additional therapeutic agents include, but are not limited to, anesthetics, antibacterial compounds, antiviral compounds, antifungal compounds, immunosuppressants, anti-inflammatory compounds, anti-proliferative compounds, anti-angiogenesis compounds, or hormones.

In some embodiments, the biocompatible hydrogel polymer or in vivo gelling pre-formulations further comprise a visualization agent for visualizing the placement of the biocompatible hydrogel polymer at a target site The visualization agent assists in visualizing the placement using minimally invasive delivery, e.g., using an endoscopic device. In certain embodiments, the visualization agent is a dye. In specific embodiments, the visualization agent is colorant.

In some embodiments, the biocompatible hydrogel polymer formulations further comprise a contrast agent for visualizing the hydrogel formulation and locating a tumor using e.g., X-ray, fluoroscopy, or computed tomography (CT) imaging. In certain embodiments, the contrast agent is radiopaque. In some embodiments, the radiopaque material is selected from sodium iodide, potassium iodide, barium sulfate, VISIPAQUE®, OMNIPAQUE®, or HYPAQUE®, tantalum, and similar commercially available compounds, or combinations thereof.

Exemplary Kits

Further provided herein is a kit comprising a) a water soluble first compound comprising more than one nucleophilic group, and an anticancer agent in an aqueous buffer; and b) a water soluble second compound comprising more than one electrophilic group; wherein a biocompatible hydrogel polymer is formed following mixing the first compound and the second compound in the aqueous buffer.

Also provided here is a kit comprising a) a water soluble first compound comprising more than one electrophilic group, and an anticancer agent in an aqueous buffer; and b) a water soluble second compound comprising more than one nucleophilic group; wherein a biocompatible hydrogel polymer is formed following mixing the first compound and the second compound in the aqueous buffer.

Further provided herein is a kit for preparing any in vivo gelling pharmaceutical pre-formulation as described herein, comprising a first container with a first amount of the first compound, a second container with a second amount of the second compound, a third container with a third amount of the anticancer agent, a fourth container with the aqueous buffer, a mixing vessel, optionally a fifth container with the radiopaque material, instructions for mixing the materials present in each container in the mixing vessel to produce the biocompatible hydrogel polymer, and instructions for delivering the biocompatible hydrogel polymer to the site of the cancer.

Also provided herein is a kit for preparing any in vivo gelling pharmaceutical pre-formulation as described herein, comprising a first container comprising a first amount of the first compound and a second amount of the anticancer agent, a second container with a third amount of the second compound, a third container with the aqueous buffer, a mixing vessel, optionally a fourth container with the radiopaque material, instructions for mixing the materials present in each container in the mixing vessel to produce the biocompatible hydrogel polymer, and instructions for delivering the biocompatible hydrogel polymer to the site of the cancer.

Further provided herein is a kit for preparing any in vivo gelling pharmaceutical pre-formulation as described herein, comprising a first container comprising a first amount of the first compound, a second container with a second amount of the second compound and a third amount of the anticancer agent, a third container with the aqueous buffer, a mixing vessel, optionally a fourth container with the radiopaque material, instructions for mixing the materials present in each container in the mixing vessel to produce the biocompatible hydrogel polymer, and instructions for delivering the biocompatible hydrogel polymer to the site of the cancer.

Additionally provided herein is a kit for preparing an in vivo gelling pharmaceutical pre-formulation comprising (a) a first container with a first amount of the at least one first compound; (b) a second container with a second amount of the at least one second compound; (c) a third container with the aqueous buffer; (d) a mixing vessel; (e) optionally, a fourth container with a third amount of one or more therapeutic agent; (f) optionally, a fifth container with the radiopaque material or dye; and instructions for mixing the materials present in each container in the mixing vessel to produce the biocompatible hydrogel polymer, and instructions for delivering the biocompatible hydrogel polymer to the target site inside the human body. In certain embodiments, the first container and the second container each are a syringe, wherein the plungers of the syringes are interconnected, and the outlets of the two syringes are connected to the mixing vessel. In some embodiments, the mixing vessel is connected to a catheter attached to an endoscopic device.

EXAMPLES

The following specific examples are to be construed as merely illustrative, and not limitative of the remainder of the disclosure in any way whatsoever.

TABLE 1

| Components used in formulations. | |
|---|---|
| Components | Technical Name |
| 4ARM-20k-AA | 4armPEG Acetate Amine HCL Salt, MW 20000 |
| 8ARM-20k-NH2 | 8arm PEG Amine (hexaglycerol), HCl Salt, MW 20000 |
| 8ARM-15k-SG | 8arm PEG Succinimidyl Glutarate (hexaglycerol), MW 15000 |
| ETTMP-1300 | Ethoxylated trimethylolpropane tri(3-mercaptopropionate) |
| EJ-190 | Sorbitol polyglycidyl ether |
| 4ARM-20k-SGA | 4arm PEG Succinimidyl Glutaramide (pentaerythritol), MW 20000 |
| DDP | cisplatin; cisdiamminedichloroplatinum(II) |
| DCP | carboplatin; cis-Diammine (1,1-cyclobutanedicarboxylato)platinum(II) |

Example 1: Manufacture of Hydrogel (Amine-Ester Chemistry)

A solution of 8ARM-20K-NH2 was prepared in a Falcon tube by dissolving about 0.13 g solid monomer in about 2.5 mL of sodium phosphate buffer (buffer pH 7.36). The mixture was shaken for about 10 seconds at ambient temperature until complete dissolution was obtained. The Falcon tube was allowed to stand at ambient temperature. In another Falcon tube, 0.10 g of 8ARM-15K-SG was dissolved in the same phosphate buffer as above. The mixture was shaken for about 10 seconds and at this point all the powder dissolved. The 8ARM-15K-SG solution was poured immediately into the 8ARM-20K-NH2 solution and a timer was started. The mixture was shaken and mixed for about 10 seconds and a 1 mL solution of the mixture was pipetted out using a mechanical high precision pipette. The gel time of 1 mL liquid was collected and then verified with the lack of flow for the remaining liquids. The get time data of the formulation was recorded and was about 1 min 30 seconds.

Example 2: Manufacture of Hydrogel (Amine-Ester Chemistry)

A solution of 8ARM-20K—NH2 was prepared in a Falcon tube by dissolving about 0.13 g solid monomer in about 5 mL of sodium phosphate buffer (buffer pH 7.36). The mixture was shaken for about 10 seconds at ambient temperature until complete dissolution was obtained. The Falcon tube was allowed to stand at ambient temperature. To this solution, 0.10 g of 8ARM-15K-SG was added. The mixture was shaken to mix for about 10 seconds until all the powder dissolved. 1 mL of the mixture was pipetted out using a mechanical high precision pipette. The gel time of the formulation was collected using the process described above. The gel time was about 1 min 30 seconds.

Example 3: Manufacture of Hydrogel (Thiol-Ester Chemistry)

A solution of ETTMP 1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.10 g of 8ARM-15K-SG was added. The mixture was shaken for about 10 seconds until the powder dissolved. 1 mL of the mixture was pipetted out using a mechanical high precision pipette. The gel time was found to be about 3 seconds.

Example 4: Manufacture of Hydrogel (Thiol-Epoxide Chemistry)

A solution of ETTMP 1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.10 g of EJ-190 was added. The mixture was shaken for about 10 seconds until complete dissolution is obtained. 1 mL of the mixture was pipetted out using a mechanical high precision pipette. The gel time was found to be about 6 minutes.

Example 5: Manufacture of Hydrogel Comprising a Therapeutic Agent

In a syringe (Syringe A), about 3 mL of a sodium phosphate buffer (buffer pH 7.36) was measured. About 25 mg of 8ARM-20k-NH2 amine was weighed in a weighing boat and placed as powder in another syringe (Syringe B). About 150 mg of the biodegradable amine 4ARM-20k-AA was weighed in a weighing boat and also placed as a powder in Syringe B. About 4.2 mg cisplatin (or about 45 mg of carboplatin) was weighed in a weighing boat and also placed as a powder in Syringe B. After adding the plunger to Syringe B, the powder contents were mixed. About 75 mg of the ester 8ARM-15k-SG was weighed in a weighing boat and placed as a powder into another syringe (Syringe C).

Syringes A and B containing the buffer and the amine/drug powder, respectively, were connected via a mixing tube. The plunger of the Syringe A (containing the buffer) was pressed until the liquid content was completely transferred to Syringe B (containing the amine/drug). Then the plunger of Syringe B was pressed such that the fluid mixture transfers back to Syringe A. This procedure was repeated until the solids were dissolved. Typically, complete dissolution was achieved in 5 to 10 passes, or approximately 5 to 10 seconds.

The empty syringe was removed from the mixing tube and replaced with Syringe C (containing the ester). Once Syringe C (containing the ester) had been connected to the mixing tube, the timer was started. Immediately, the mixing process was started by pressing the syringe plunger of Syringe B to mix the contents of Syringes C and B. The contents of Syringe C were dissolved in the same fashion as described above. The gel time was measure as described in EXAMPLE 1. The gel time was approximately 90 seconds.

Example 6: In Vitro Bioabsorbance Testing

A 0.10 molar buffer solution of pH 7.40 was prepared with deionized water. A 50 mL portion of this solution was transferred to a Falcon tube. A sample polymer was prepared in a 20 cc syringe. After curing, a 2-4 mm thick slice was cut from the polymer slug and was placed in the Falcon tube. A circulating water bath was prepared and maintained at 37° C. The Falcon tube with polymer was placed inside the water bath and time was started. The dissolution of the polymer was monitored and recorded. The dissolution time ranged from 1-90 days depending on the type of sample polymer.

Example 7: Gelling and Degradation Times

The amine-ester materials explored included: 4ARM-20k-AA/8ARM-20k-NH2 (where x/y is the molar ratio of equivalent functional amine groups of 4ARM-20k-AA to 8ARM-20k-NH2) with an amount of equivalent ester 8ARM-15k-SG present in the sum of x and y; and 4ARM-20k-AA/8ARM-20k-NH2 (50/50) with an alternative ester 4ARM-20k-SGA. Previous results demonstrated the increase in degradation time with a decreasing amount of biodegradable amine (4ARM-20k-AA) and varying the amount of this amine influences the gel and degradation times. The 4ARM-20k-AA/8ARM-20k-NH2 (50/50) formulation was used to load either cisplatin (DDP) or carboplatin (DCP). The alternative ester (4ARM-20k-SGA) was studied in the 4ARM-20k-AA/8ARM-20k-NH2 formulation because it possessed a similar chemical structure to that of the 8ARM-15k-SG ester, but lacks certain hydrolysable moieties that increase the degradation time.

The thiol-ester material explored involved ETTMP-1300, which was the thiol present in either 2/1 or 1/1 molar ratio of equivalent functional groups of thiol to ester. The thiol-ester formulation was evaluated with DDP and DCP to determine whether fundamental polymer properties remained unchanged, since the reactivity of platinum complexes with thiols was well documented in the literature.

Finally, the 4ARM-20k-AA/8ARM-20k-NH2 (50/50) formulation was used to study the effect of mixing time since the polymer formation depends on the dissolution of multiple solids into solution.

Raw Materials & Instrumentation

All reagents were commercially available and used without further purification. The amines and esters (4ARM-20k-AA, 8ARM-20k-NH2, 8ARM-15k-SG, and 4ARM-20k-SGA) were custom synthesized by JenKem Technology and stored under a nitrogen atmosphere. The thiol used (ETTMP-1300) was a trade sample from Chemische Fabrik GmbH&Co., and was stored under a nitrogen atmosphere. DDP and DCP were purchased from Sigma Aldrich and handled in a LabConco Precise HEPA-filtered glove box. For the degradation studies, a Premiere Digital Water Bath Model HH-4 was used to maintain a constant temperature of 36.5° C. The thiol and platinum compounds were weighed to an accuracy of 0.1 mg, while the amines and esters were weighed to an accuracy of 5 mg. A 0.05 M sodium phosphate buffer with a pH between 7.2 and 7.4 was prepared and used for all procedures where indicated. Two 0.05 M sodium borate buffers were prepared with a pH of either 7.94 or 8.35 and used where indicated.

Gel and Degradation Times

The gel time for all experiments was measured starting from the addition of the ester (8ARM-15k-SG or 4ARM-20k-SGA) until the solidification of the solution, which was observed by the absence of fluid motion upon tilting the tube horizontally. Degradation of the polymers was performed by the addition of 5 mL phosphate buffer to 5 g of the material in a 50 mL centrifuge tube and incubating the mixture at 36.5° C. The degradation time was measured starting from the day of addition of the phosphate buffer to complete dissolution of the polymer into solution.

Formulation of Amine-Ester Polymers

The 4ARM-20k-AA and 8ARM-20k-NH2 (typically in the range of 0.1 mmol arms equivalents) was intimately mixed in a 50 mL centrifuge tube. A volume of phosphate buffer was added to the tube via a micropipette such that the final percent of solids in solution was 5 percent. The mixture was shaken briefly before adding the appropriate amount of ester (8ARM-15k-SG). Immediately after adding the ester, the entire solution was shaken for 5 to 10 seconds before letting it rest. 4ARM-20k-AA/8ARM-20k-NH2 molar ratios of 75/25, 60/40, 55/45 and 50/50 were studied (Table 2).

A similar procedure was followed for the formulation of the 4ARM-20k-AA/8ARM-20k-NH2 (50/50) polymer with the alternative ester 4ARM-20k-SGA (Table 3).

TABLE 2

Gel and degradation times for varying 4ARM-20k-AA/8ARM-20k-NH2 ratios with 8ARM-15k-SG ester.

| | 4ARM-20k-AA/8ARM-20k-NH2 | Gel Time (min) | Degradation Time (days) |
|---|---|---|---|
| 1 | 100/0 | 1.30 | 2 to 4 |
| 2 | 75/25 | 1.46 | 5 to 7 |
| 4 | 60/40 | 1.33 | 5 to 7 |
| 5 | 55/45 | 1.33 | 11 to 13 |
| 6 | 50/50 | 1.50 | 15-20 |
| 7 | 0/100 | 1.30 | 56-62 |

TABLE 3

Gel and degradation times for the 4ARM-20k-AA/8ARM-20k-NH2 (50/50) formulation with the new ester (4ARM-20k-SGA)

| 4ARM-20k-AA/8ARM-20k-NH2 | Gel Time (min) | Degradation Time (days) |
|---|---|---|
| 50/50 | 2.50 | >14 |

It was found that decreasing the molar ratio of 4ARM-20k-AA/8ARM-20k-NH2 from 75/25 to 50/50 had no significant effect on gel time, but increased the degradation time from about 6 days to about 15 days. The gel and degradation times of the 4ARM-20k-AA/8ARM-20k-NH2 (50/50) formulation with the alternative ester 4ARM-20k-SGA demonstrated that the degradation time has been prolonged by an as yet undetermined number of days and that the gel time has increased by about one minute.

The data presented in Table 2 demonstrate that the degradation time can be controlled by the 4ARM-20k-AA/8ARM-20k-NH2 ratio.

Formulation of Thiol-Ester Polymers

A volume of borate buffer of a certain pH (pH of 7.94 or 8.35) was added to a 50 mL centrifuge tube via a micropipette such that the final percent of solids in solution was 5 percent. ETTMP-1300 (typically in the range of 0.1 mmol arms equivalents) was dissolved in the buffer with brief shaking. Then, the appropriate amount of ester (8ARM-15k-SG) was added and the entire solution was shaken for 5 to 10 seconds before letting it rest. ETTMP-1300 to 8ARM-15k-SG molar ratios of 2/1 and 1/1 were studied (Table 4).

TABLE 4

Gel time for the ester/thiol (1/1) formulation
with two borate buffers of differing pH.

| Borate Buffer ID | pH | Gel Time (min) |
| --- | --- | --- |
| SA-01-17A | 7.94 | 5.00 |
| SA-01-18A | 8.35 | 1.75 |

It was observed that the relatively long gel time of about 5 minutes was significantly decreased to less than 2 minutes by increasing the pH of the borate buffer from 7.94 to 8.35.

The data presented in Table 4 demonstrate that the gel time is controlled by the pH of the buffer. Furthermore, experiments showed that the thiol-ester chemistry required a borate buffer and a higher pH than the amine-ester chemistry, since a phosphate buffer with similar pH did not show any significant polymerization reaction at comparably low pH.

Formulation of Polymers with DDP and DCP

A saturated solution of DDP or DCP in the phosphate and borate buffers was created at 25° C. The final concentration of DDP was 1.3 mg/mL in both the phosphate buffer and borate buffer (pH of 7.94), while the final concentration of DCP was 14.7 mg/mL in the phosphate buffer and 15.6 mg/mL in the borate buffer (pH of 7.94). The amine- and thiol-ester polymers were formulated in the same fashion as previously described, but with the appropriate DDP or DCP buffer solution (Table 5 and Table 6). Samples containing DDP or DCP were protected from light as a precaution.

TABLE 5

Gel and degradation times for the 4ARM-20k-AA/8ARM-20k-NH2
(50/50) formulation with 8ARM-15k-SG ester and DDP or DCP.

| 4ARM-20k-AA/<br>8ARM-20k-NH2 (50/50) | Gel Time (min) | Degradation Time (days) |
| --- | --- | --- |
| DDP | 1.5 | 11 to 14 |
| DCP | 1.5 | >11 |

TABLE 6

Gel and degradation times for the ester/thiol (1/2) formulation
with 8ARM-15k-SG ester and DDP or DCP.

| Ester/Thiol (1/2) | Gel Time (min) | Degradation Time (days) |
| --- | --- | --- |
| DDP | 5.33 | >14 |
| DCP | 4.33 | >2 |

The data presented in Table 5 and Table 6 demonstrate that the loading of DDP or DCP into the above formulations appears to have no significant effect on gel and degradation times.

Mixing Time

The mixing time was measured for the 4ARM-20k-AA/8ARM-20k-NH2 (50/50) formulation starting from the addition of the 8-ARM-SG ester and the commencement of shaking the mixture. Gel times were measured for mixing times of 1, 5, 10 and 45 seconds.

TABLE 7

Effect of mixing time on the gel time of the 4ARM-20k-AA/
8ARM-20k-NH2 (50/50) formulation with 8ARM-15k-SG ester.

| Mixing Time (s) | Gel Time (min) | |
| --- | --- | --- |
| 1 | 2.33 | |
| 5 | 1.92 | |
| 10 | 1.50 | (2× scale of other data points) |
| 45 | 2.00 | |

The data presented in Table 7 showing the effect of component mixing time on gel time for the 4ARM-20k-AA/8ARM-20k-NH2 (50/50) formulation with 8ARM-15k-SG ester suggests that a sufficient mixing time is between 5 and 10 seconds, and that further mixing has little effect on gel time.

Example 8: Drug Elution from Amine-Ester Hydrogel

Figure 2:
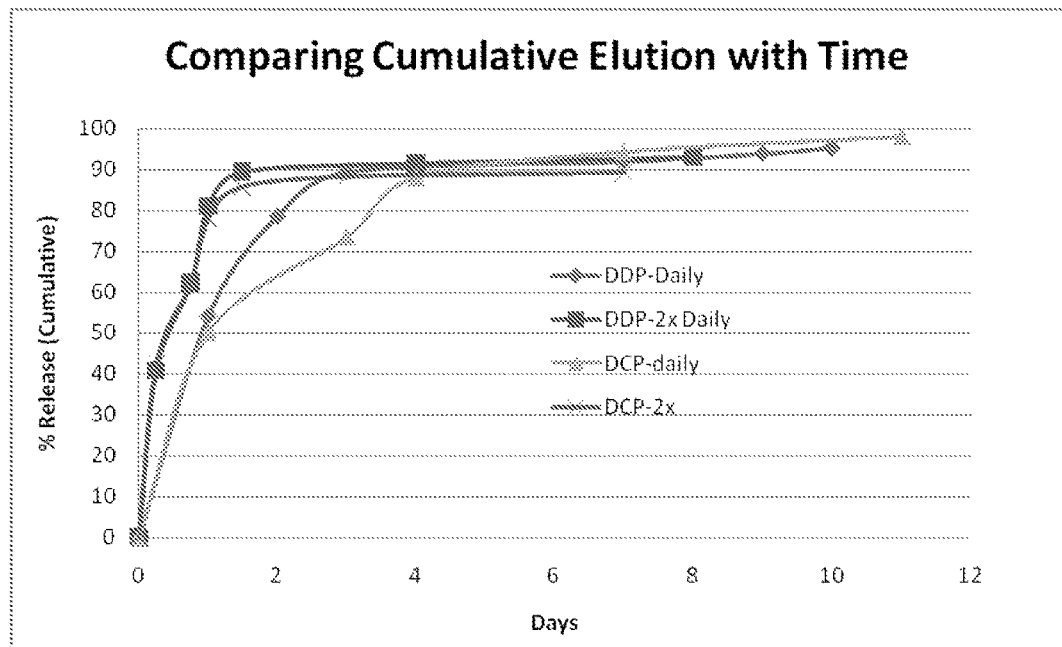
FIG. 2 shows the cumulative elution of carboplatin and cisplatin in PBS buffer using one buffer change per day (daily) or two buffer changes per day (2× daily).

The hydrogel was prepared as described in EXAMPLE 5 using the 4ARM-20k-AA/8ARM-20k-NH2 (50/50) formulation with 8ARM-15k-SG ester and DDP or DCP. Two extraction methods were used: In extraction method 1 one buffer change every 24 hours was performed with 1 mL buffer per gram of polymer; in extraction method 2 two buffer changes were performed per 24 hour period for two days and then one buffer change every 24 hours. The data presented in FIG. 1 and FIG. 2 demonstrate that the in vitro elution kinetics depend on the extraction method, wherein more frequent extraction results in faster elution. Cisplatin and carboplatin have slightly different elution kinetics, but most of the drugs elutes from the polymer with more than 40% of the drugs eluted after one day using either drug.

Example 9: Preparation of Biocompatible Hydrogel Polymer Comprising Docetaxel

The in vivo gelling pharmaceutical pre-formulation forming a biocompatible hydrogel is prepared according to the procedure in EXAMPLE 5, but using docetaxel instead of carboplatin or cisplatin.

Example 10: Preparation of Biocompatible Hydrogel Polymer Comprising Paclitaxel

The in vivo gelling pharmaceutical pre-formulation forming a biocompatible hydrogel is prepared according to the procedure in EXAMPLE 5, but using paclitaxel instead of carboplatin or cisplatin.

Example 11: Preparation of Biocompatible Hydrogel Polymer Comprising Oxaliplatin The in vivo gelling pharmaceutical pre-formulation forming a biocompatible hydrogel is prepared according to the procedure in EXAMPLE 5, but using oxaliplatin instead of carboplatin or cisplatin.

Example 12: Preparation of Biocompatible Hydrogel Polymer Comprising Satraplatin The in vivo gelling pharmaceutical pre-formulation forming a biocompatible hydrogel is prepared according to the procedure in EXAMPLE 5, but using satraplatin instead of carboplatin or cisplatin.

Example 13: Preparation of Biocompatible Hydrogel Polymer Comprising Gemcitabine The in vivo gelling pharmaceutical pre-formulation forming a biocompatible hydrogel is prepared according to the procedure in EXAMPLE 5, but using gemcitabine instead of carboplatin or cisplatin.

Example 14: Preparation of Biocompatible Hydrogel Polymer Comprising Pemetrexed

The in vivo gelling pharmaceutical pre-formulation forming a biocompatible hydrogel is prepared according to the procedure in EXAMPLE 5, but using pemetrexed instead of carboplatin or cisplatin.

Example 15: Preparation of Biocompatible Hydrogel Polymer Comprising Temozolomide The in vivo gelling pharmaceutical pre-formulation forming a biocompatible hydrogel is prepared according to the procedure in EXAMPLE 5, but using temozolomide instead of carboplatin or cisplatin.

Example 16: Preparation of Biocompatible Hydrogel Polymer Comprising Doxorubicin The in vivo gelling pharmaceutical pre-formulation forming a biocompatible hydrogel is prepared according to the procedure in EXAMPLE 5, but using doxorubicin instead of carboplatin or cisplatin.

Example 17: Preparation of Biocompatible Hydrogel Polymer Comprising Diphtheria Toxin The in vivo gelling pharmaceutical pre-formulation forming a biocompatible hydrogel is prepared according to the procedure in EXAMPLE 5, but using diphtheria toxin instead of carboplatin or cisplatin.

Example 18: Preparation of Biocompatible Hydrogel Polymer Comprising α-Hemolysin The in vivo gelling pharmaceutical pre-formulation forming a biocompatible hydrogel is prepared according to the procedure in EXAMPLE 5, but using α-hemolysin instead of carboplatin or cisplatin.

Example 19: Preparation of Biocompatible Hydrogel Polymer Comprising Ciclosporin The in vivo gelling pharmaceutical pre-formulation forming a biocompatible hydrogel is prepared according to the procedure in EXAMPLE 5, but using ciclosporin instead of carboplatin or cisplatin.

Example 20: Delivery of Pre-Formulation Into Rabbit Lungs

The goal of the experiment was to test the delivery of a biocompatible hydrogel polymer into the rabbit lung by bronchoscopy. In addition, the safety of the biocompatible hydrogel polymer and the ability of the polymer to stay localized were assessed. Furthermore, changes in histology due to the polymer were evaluated.

Three adult New Zealand rabbits (~5 lbs) and an Olympus bronchoscope BF XP-160F (2.8 mm×600 mm, 1.2 mm working channel) were used in the study. The in vivo gelling pharmaceutical pre-formulation was selected to have an approximately 90 second gel time and a more than 60 days degradation time. The pre-formulation and the saline control comprised about 10% weight/volume barium sulfate for visualization. The rabbits were infused with about 3 mL of pre-formulation or saline solution followed by 7 mL of air.

Two rabbits received the in vivo gelling pharmaceutical pre-formulation, and 1 rabbit received saline as a control. All rabbits survived the entire study period of 15 days. No respiratory difficulty was observed during the study. It was possible to instill solutions in the right middle lobe (RML) in all rabbits without difficulty. The study used approximately 10-times more barium sulfate and 3-times more polymer than what was actually needed. All solutions stayed localized in the RML, including the saline control, mainly because the high concentration of barium sulfate increased the viscosity of the control solution.

In the first rabbit, the pre-formulation was injected rapidly, within about 30-40 seconds. A CT on day 1 showed small right pneumothorax, which was resolved by day 4. The biocompatible hydrogel polymer stayed localized for the entire study. On gross pathology, a thick pleural capsule was observed around the RML. Histology revealed that the polymer distributed into the alveoli although somewhat patchy. Some areas of necrosis and pleura thickening were observed. Upon review, the injection pressure was too high in this study rabbit, causing a bronchopleural fistula (BPF) with pneumothorax and patchy distribution of the polymer. The polymer appeared to have sealed the BPF and the pneumothorax resolved within 4 days, allowing the rabbit to survive for the whole 15 day study period.

For the second rabbit, there was some difficulty with getting the polymer ready for injection, which resulted in a delay in polymer injection as compared to the first rabbit. Some polymer actually gelled on the tip of the bronchoscope, but was easily wiped off with gauze. Some polymer was seen stuck onto the tracheal wall, probably after being brushed on as the bronchoscope was pulled out. Efforts to suction the polymer off the tracheal wall were unsuccessful, as the polymer appeared to adhere fairly well to the tissue. Gross pathology showed an even distribution of the polymer in the alveoli. Histology showed a preserved lung architecture and no necrosis. Furthermore, giant cells and granulomas had formed, but no fibrosis or necrosis was observed and the pleura was intact with slightly thickened alveolar membrane but no destruction of the capillaries. These observations show that the polymer should be administered using a low injection pressure.

In the rabbit given the saline control solution, the addition of barium sulfate created a somewhat thick, final solution at baseline with an increased viscosity due to the barium sulfate. After instillation, some barium sulfate/saline solution was seen welling out of the RML bronchus, which was not observed for the rabbits administered with the pre-formulation. On gross pathology, the RML was much smaller. On histology, primarily foamy macrophages and no granulomas were observed. The barium sulfate was deposited in the alveoli and was localized in the RML.

In conclusion, the pre-formulation was easy to deliver and stayed localized. It appeared to be safe, entered the alveoli and could not be coughed out. The rabbits survived large volumes of hydrogel polymer in their lungs without difficulty (3 mL of hydrogel polymer in a rabbit lung is approximately equivalent to about 180 mL in a human lung). The changes in histology due to the polymer were minor and not life threatening or serious and are expected to disappear once the polymer degrades.

Example 21: Verification of Curing Post-Administration

The hydrogel is prepared in a mixing vessel as described above. A desired amount of hydrogel is removed from the mixing vessel for delivery to the target site. Appropriate curing of the biocompatible hydrogel polymer at the target site is verified by evaluating the residual hydrogel left in the mixing vessel. A lack of flow indicates that the hydrogel is cured.

Example 22: Delivery of Hydrogel to Lung Tumor Through Bronchoscope

A rabbit model of lung cancer is created by subculturing VX2 cells derived from rabbit skin squamous cell carcinoma in the femoral muscle of a rabbit. VX2 tumors are excised, washed, and suspended in collagen gel matrix. $1 \times 10^8$ VX2 tumor cells are instilled into the right middle lobe (RML) and left lower lobes (LLL) of the rabbit lung under sedation using a pediatric bronchoscope with an outer diameter of 3.6 mm and working channel of 1.2 mm. Rabbits are imaged every 1 week using an animal CT scanner until tumor formation is detected. An in vivo gelling pharmaceutical pre-formulation comprising a chemotherapeutic anticancer agent (e.g., cisplatin) is delivered to the RML tumor only using a pediatric bronchoscope with 1.2 mm outer diameter catheter inserted through the working channel to deliver the pre-formulation. Tumor size is measured by CT imaging every 5-7 days. Tumor volume is measured by semi-automatic segmentation using active contour methods with the program ITK-SNAP. Tumor size of the treated RML tumor is directly compared to the tumor size of the untreated LLL tumor in the same animal. Rabbits are closely monitored for any side effects from biocompatible hydrogel polymer delivery. At the end of the study, rabbits are euthanized and necropsies are performed for detailed histological and pathologic analysis of the lung and lung cancers.

Example 23: Elution Kinetic of Drugs in Rabbit Model

Rabbits with specific doses of a biocompatible hydrogel polymer delivered into the lung by bronchoscopy have blood drawn at time intervals 30 min, 1 hour, 2 hours, 3 hours, 6 hours, 12 hours, 24 hours, 48 hours, 5 days, 10 days, 20 days, and 30 days for measurement of therapeutic agent drug levels in the serum. These blood draws are performed in different rabbits at different therapeutic agent doses to generate drug absorption and drug elution curves for the biocompatible hydrogel polymer. Serum drug levels are measured by high-performance liquid chromatography (HPLC) or other quantitative methods.

Example 24: Clinical Trial for the Treatment of Lung Cancer

The study goal is to evaluate the safety and efficacy of an in vivo gelling pharmaceutical pre-formulation forming a biocompatible hydrogel polymer containing cisplatin and/or carboplatin in the treatment of primary lung malignancies and pulmonary metastases. The study endpoints are local tumor control and lack of adverse events.

The inclusion criteria for admittance to the study are patients with one or more primary or secondary lung malignancies who are not candidates for or reject surgical resection, having a Karnofsky Index of >70%, and are not requiring home oxygen. The patient population for the study is 30 male and female patients.

Prior to treatment, CT thorax is obtained within 2 weeks of the procedure and the tumor is identified. Bronchoscopy is performed in the outpatient setting under conscious sedation with IV fentanyl and midazolam in incremental doses. The bronchoscope is navigated to the area of the tumor identified on CT with either visual guidance only or visual guidance plus electromagnetic navigational guidance (at the discretion of the operator). The cisplatin or carboplatin pre-formulation (30 mL) is instilled in the appropriate area of the lung through a catheter inserted through the working channel of the bronchoscope over 45-60 seconds. Blood is drawn within 2 hours after the procedure to measure serum cisplatin or carboplatin levels, chemistry panel, and blood count. The patient is discharged home after the procedure.

Follow-up clinical examination is performed at day 1, day 7, day 30, and every 12 weeks after the procedure for an intended follow-up period of 2 years. Each clinical visit is accompanied by blood sampling. CT thorax is performed at day 30, week 12, and every 6 months for total of 2 years.

Remission criteria and local control rates after treatment with the biodegradable hydrogel polymer are defined according to modified WHO response criteria for solid tumors and represents either stable disease (SD), partial (PR) or complete remission (CR) of the treated lesion. Any increase >20% in diameter of a singular lesion is interpreted as progression.

Example 25: Clinical Trial for the Treatment of Mesothelioma

The study goal is to evaluate the safety and efficacy of a intrapleurally infused in vivo gelling pharmaceutical pre-formulation forming a biocompatible hydrogel polymer containing cytotoxin or a chemotherapeutic anticancer agent in patients with malignant pleural mesothelioma (MPM) localized to one hemithorax. The study endpoints are local tumor control and lack of adverse events.

The inclusion criteria for admittance to the study are patients with histologically confirmed MPM who are not candidates for or reject other treatment options (chemotherapy, extrapleural pneumonectomy, radiation therapy), having a Karnofsky Index of >60% and for whom preventive radiotherapy of the point of entry of the thoracoscope is recommended. The patient population for the study is 15 male and female patients.

Prior to treatment, CT thorax is obtained within 2 weeks of the procedure and the extent of MPM identified. Thoracoscopy is performed in the operating room under general anesthesia and any effusion is drained. An in vivo gelling pharmaceutical pre-formulation comprising cytotoxin or an anticancer agent (50 to 100 mL) are sprayed onto the areas of MPM identified by thoracoscopy. Blood is drawn within 2 hours after the procedure to measure serum anticancer agent or cytotoxin levels, chemistry panel, and blood count. The patient is hospitalized for at least 3 days after the procedure to ensure complete recovery.

Follow-up clinical examination is performed at day 1, day 3, day 14, and every 8 weeks after the procedure for an intended follow-up period of 1 year. Each clinical visit is accompanied by blood sampling. CT thorax is performed at day 14, week 8, and every 3-4 months for a total of 1 year.

Remission criteria and local control rates after treatment are defined according to modified RECIST criteria for MPM based on tumor thickness perpendicular to the chest wall or mediastinum. Patients are characterized as having stable disease (SD), partial remission (PR), or complete remission (CR). Any increase >20% in total tumor measurement or appearance of new lesions is interpreted as progression.

Example 26: Clinical Trial for the Treatment of Bronchopleural Fistula

Patients with a post-pneumonectomy or post-lobectomy bronchopleural fistula (BPF) are treated by bronchoscopic injection of an in vivo gelling pharmaceutical pre-formulation forming a biocompatible hydrogel polymer. The patients are also treated with a chest drain. All patients have undergone lung resection for cancer and present an early fistula. The bronchial stump has been closed by a mechanical stapler or sutures in all patients.

According to the modified classification of Le Brigand, fistulas are considered early if occurring within 1-7 days after lung resection. The occurrence of fistula is from 3 to 7 days after the operation (mean: 5.6 days). The diameter of the fistula is between 3-10 mm. All patients are examined by computed tomography (CT) of the chest and bronchoscopy. In all patients, a chest drain is inserted at the time of fistula diagnosis.

Endoscopic treatment consists of repeated (once every 48 h for a maximum of five applications) injections of the in vivo gelling pharmaceutical pre-formulation forming a biocompatible polymer on the margins of the fistula. All procedures are performed using a flexible bronchoscope with an operative channel. When the in vivo gelling pharmaceutical pre-formulation is ready, an endoscopic catheter is advanced through the operative channel of the flexible bronchoscope and several deliveries of the pre-formulation are performed at the margins of the fistula under direct vision. A maximum of five endoscopic applications for each patient is planned. In case of persistent fistula after the fifth application, surgical repair would subsequently be planned.

The chest drain is removed after the disappearance of air leaks if bronchoscopy shows a complete resolution of the fistula.

What is claimed is:

1. A method of treating a lung disease in a mammal, comprising delivering a biocompatible hydrogel polymer to a target site in the lung of the mammal, wherein the biocompatible hydrogel polymer gels to at the target site in the lung and wherein the biocompatible hydrogel polymer consists of an aqueous buffer, a therapeutic agent, and a polymer prepared from monomers consisting of:
   (a) 8-ARM-20k-NH2 PEG amine, 4-ARM-20k-AA acetate amine, and 8-ARM-PEG-SG monomer; or
   (b) 8-ARM-20k-NH2 PEG amine, 8-ARM-20k-AA acetate amine, and 8-ARM-PEG-SG monomer and wherein the biocompatible hydrogel polymer dos not contain blood or protein.

2. The method of claim 1, wherein the lung disease is a cancer of a lung, wherein the target site in the lung of the mammal is a site of the cancer of the lung, and wherein the therapeutic agent is an anticancer agent.

3. The method of claim 1, wherein the lung disease is mesothelioma, wherein the target site in the lung of the mammal is a site of the mesothelioma, and wherein the therapeutic agent is an anticancer agent.

4. The method of claim 1, wherein the lung disease is emphysema, wherein the target site in the lung of the mammal is a site affected by the emphysema, wherein the therapeutic agent is an antiviral agent, antibacterial agent, antifungal agent, immunosuppressant agent, or anti-inflammatory agent, wherein the biocompatible hydrogel polymer blocks an air passage or changes the lung surface tension, and wherein a portion of the lung is controllably collapsed.

5. The method of claim 1, wherein the lung disease is a bronchopleural fistula, wherein the target site in the lung of the mammal is a site of a fistula in the lung of the mammal, wherein the therapeutic agent is an antiviral agent, antibacterial agent, antifungal agent, immunosuppressant agent, or anti-inflammatory agent, wherein the biocompatible hydrogel polymer gels at the site of the fistula, and wherein the biocompatible hydrogel polymer seals the fistula.

6. The method of claim 2, wherein the anticancer agent is selected from the group consisting of docetaxel, paclitaxel, carboplatin, cisplatin, oxaliplatin, satraplatin, etoposide, gemcitabine, pemetrexed, diphtheria toxin, adenylate cyclase toxin, verotoxin-1, α-toxin, α-hemolysin, curare, and α-cobratoxin.

7. The method of claim 3, wherein the anticancer agent is selected from the group consisting of docetaxel, paclitaxel, carboplatin, cisplatin, oxaliplatin, satraplatin, etoposide, gemcitabine, pemetrexed, diphtheria toxin, adenylate cyclase toxin, verotoxin-1, α-toxin, α-hemolysin, curare, and α-cobratoxin.

8. The method of claim 1, wherein the biocompatible hydrogel polymer does not contain biological materials.

9. The method of claim 1, wherein the biocompatible hydrogel gels to at the target site in the lung and has a degradation time of more than 60 days.

* * * * *